United States Patent [19]
Gerber et al.

[11] Patent Number: 5,517,234
[45] Date of Patent: May 14, 1996

[54] AUTOMATIC OPTICAL INSPECTION SYSTEM HAVING A WEIGHTED TRANSITION DATABASE

[75] Inventors: H. Joseph Gerber, West Hartford; Ronald J. Straayer, South Windsor; Bruce L. Davidson, East Hartford; Scott P. Snietka, Andover; Peter M. Walsh, South Windsor; Dana W. Seniff, South Glastonbury; James P. Kohler, Southbury, all of Conn.

[73] Assignee: Gerber Systems Corporation, South Windsor, Conn.

[21] Appl. No.: 143,434

[22] Filed: Oct. 26, 1993

[51] Int. Cl.⁶ .................. H04N 1/18; H04N 9/47
[52] U.S. Cl. .................. 348/126; 348/127; 348/125; 348/129
[58] Field of Search .................. 348/125, 127, 348/126, 129, 131

[56] References Cited

U.S. PATENT DOCUMENTS

| | | | |
|---|---|---|---|
| 4,877,326 | 10/1989 | Chadwick et al. | 348/125 |
| 5,008,743 | 4/1991 | Katzir et al. | 358/101 |
| 5,056,765 | 10/1991 | Brandstater | 269/20 |
| 5,058,982 | 10/1991 | Katzir | 385/33 |
| 5,153,668 | 10/1992 | Katzir et al. | 356/237 |
| 5,157,762 | 10/1992 | Snietka | 348/125 |
| 5,163,128 | 11/1992 | Straayer | 348/127 |
| 5,204,910 | 4/1993 | Lebeau | 348/125 |
| 5,204,912 | 4/1993 | Schimanski | 348/125 |
| 5,231,675 | 6/1993 | Sarr et al. | 348/126 |
| 5,247,585 | 9/1993 | Watanabe | 348/126 |

FOREIGN PATENT DOCUMENTS

| | | |
|---|---|---|
| 0386924 | 2/1990 | European Pat. Off. ....... H05K 13/00 |
| 91/08746 | 11/1991 | European Pat. Off. . |
| 93/00770 | 1/1993 | European Pat. Off. . |
| 93/00791 | 8/1993 | European Pat. Off. . |
| 9315474 | 8/1993 | Israel . |

*Primary Examiner*—Tommy P. Chin
*Assistant Examiner*—Anand S. Rao
*Attorney, Agent, or Firm*—McCormick, Paulding & Huber

[57] ABSTRACT

A method and apparatus used with a printed circuit board (PCB) defect detection system generates a reference database image of the PCB having tolerances for each individual PCB feature wherein a tolerance database of at least three states in which each color is weighted and adjacent pixels are grouped into arrays or "bins". An error signal is generated when the sum of the pixel weights in a bin exceeds a preselected threshold.

16 Claims, 10 Drawing Sheets

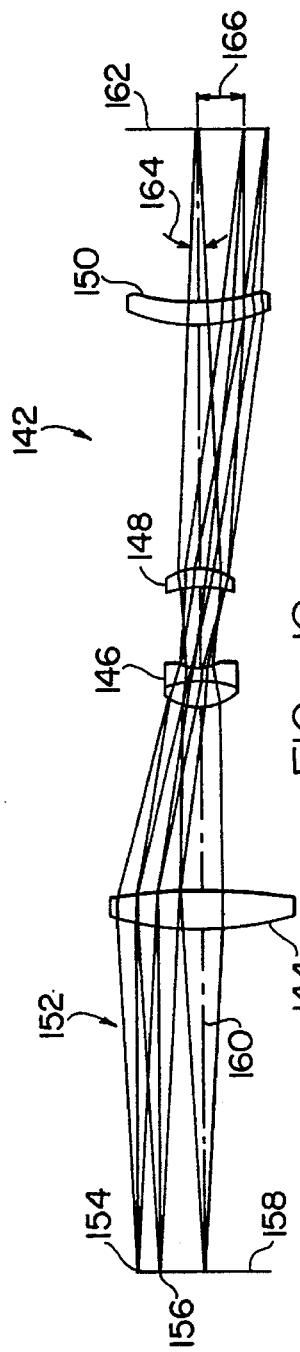
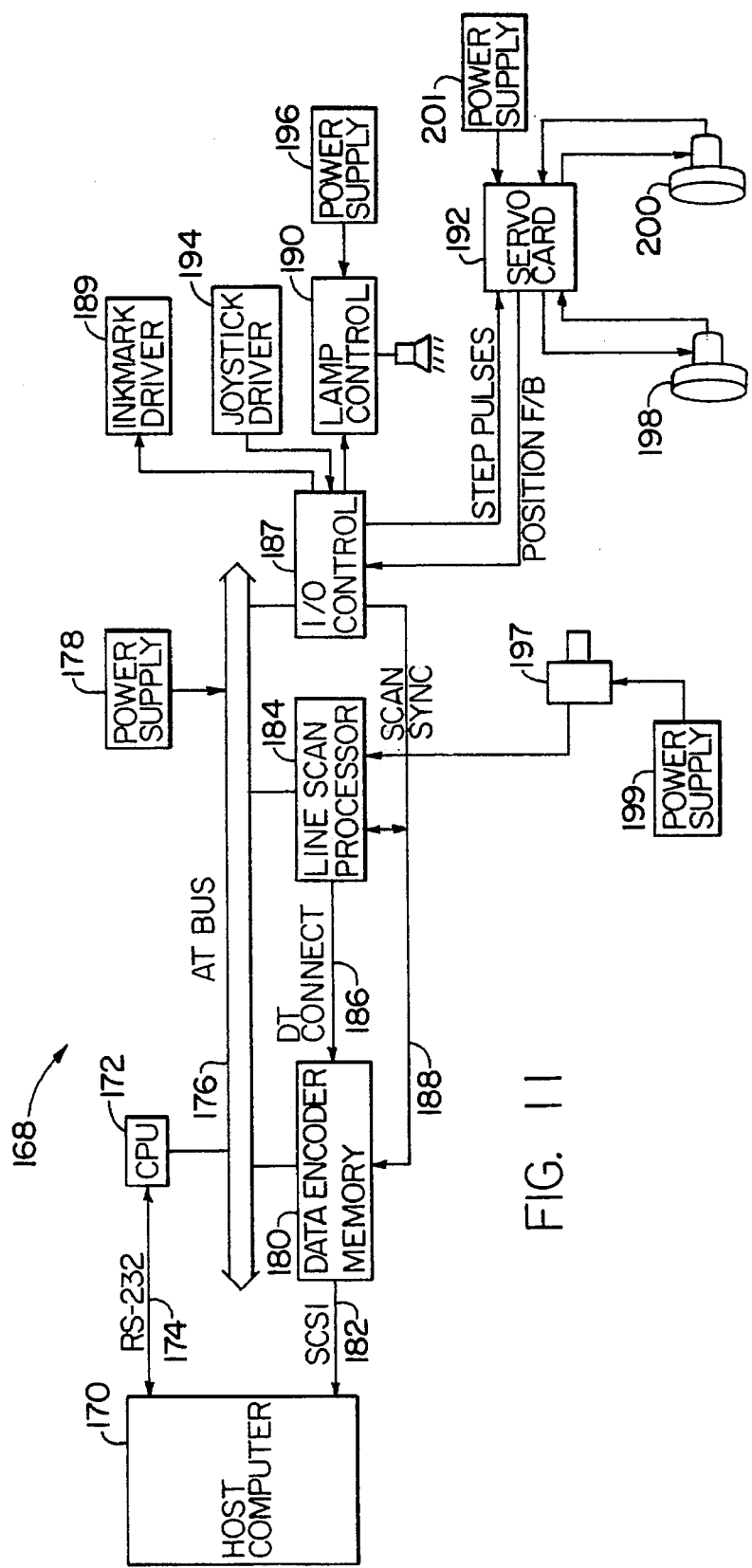
FIG. 10
FIG. 11

AUTOMATIC OPTICAL INSPECTION SYSTEM HAVING A WEIGHTED TRANSITION DATABASE

TECHNICAL FIELD

This invention relates to defect detection systems used with the production of printed circuit boards (PCB), and more particularly to a system which creates a transition data base (TDB) containing tolerance information of PCB patterns used in defect inspection of fabricated printed circuit boards wherein pixel signals are weighted by transition type.

BACKGROUND OF THE INVENTION

Printed circuit boards are today manufactured by a process which is almost completely automated. The circuits for a particular printed circuit board are generated using a computer aided design (CAD) machine which will not only generate a schematic of the printed circuit board but also will provide the board layout for all of the devices thereon. The printed circuit board layout information is provided to a device such as a laser plotter which exposes the artwork needed to fabricate the printed circuit board. The artwork comprises a series of transparent and opaque areas as features corresponding to the PCB devices.

However, defects may be present in the printed circuit board or the PCB artwork which would render the printed circuit board useless. These defects can have a variety of causes, including shrinkage in the artwork or failures in the fabrication process. Many known systems for defect detection in printed circuit boards have often simply compared a given printed circuit board against a reference, defect free printed circuit board (i.e. golden board) to detect errors created during the fabrication process. A Golden Board System does not detect errors in subsequent boards that were also in the golden board.

Moreover, some of the known optical PCB inspection systems are configured to examine inspection marks which are placed on the artwork away from the features. The dimensions and locations of the registration marks on the printed circuit board are compared against a reference to determine the extent of shrinkage. Should the shrinkage exceed a certain value, the board is considered by these systems to be defective.

In order to create an image of the PCB features, the CAD data must be translated into raster format and provided to a laser direct imager (LDI) such as the LDI 9720 or 9725 marketed by the Gerber Scientific Instrument Company, the assignee of the present invention. The comparison of devices on the printed circuit board and features on the reference image is performed by a device such as the model 1850 defect detection system, also marketed by the Gerber Scientific Instrument Company.

A technique for generating a three state transitional data base (TDB) is disclosed and claimed in the commonly owned U.S. Pat. No. 5,157,762 entitled "A Method and Apparatus for Providing a Three State Database for use with Automatic Optical Inspection Systems" and is incorporated herein by reference. That technique is characterized by an algorithm which creates from a two state database a three state (black, white, gray) TDB with each feature having a single, uniform tolerance.

Another method and apparatus used with printed circuit board (PCB) defect detection is disclosed and claimed in U.S. Pat. No. 5,163,128 and is incorporated herein by reference. The '128 system generates a reference database image of the PCB having tolerances for each individual PCB feature and is characterized by a transitional data base having three states, black, white and gray corresponding to areas where the PCB features respectively must appear, must not appear and may or may not appear.

These systems are limited in the fact that certain defects will not be found. For example, if adjacent features are separated by a distance less than the sum of the corresponding feature tolerances, a short therebetween will not be detected by known three state transition database systems since the short is coextensive with the feature tolerances.

It would be advantageous to have a method and apparatus for creating a database from the original raster CAD data for use in defect detection of printed circuit boards which would provide the capability of generating a weighted transition database allowing for more precise detection of defects. The present invention is directed towards such a method and apparatus.

SUMMARY OF INVENTION

An object of the present invention is to provide a method and apparatus for use with printed circuit board automatic optical inspection systems having the capability of generating a tolerance database wherein each state in a transition database having at least three states is weighted and wherein adjacent pixels are grouped such that a defect is indicated when the sum of transition weights for a group exceeds a threshold value.

Another object of the present invention is to provide a system of the foregoing type wherein each scanned pixel signal is compared against a corresponding database signal and given a defect weight in accordance with preset values for a given pixel state.

Still another object of the present invention is to provide a system of the foregoing type wherein pixels are designated as being of one of four states, a first state, first transition state, second transition state and second state.

Yet another object of the present invention is to provide a system of the foregoing type wherein pixels are grouped in N by N arrays yielding a total defect weight and wherein defect signals are generated if the total defect weight exceeds a threshold value.

Another object of the present invention is to provide a system of the foregoing type that performs a pixel by pixel signal comparison in compressed data signal form.

Still another object of the present invention is to provide a system of the foregoing type wherein transition pixels for each feature are directly used in the detection of a defect.

Another object of the present invention is to provide a system of the foregoing type wherein multiple cameras are used without precise alignment wherein a series of marks on a reference substrate of known separation are scanned and a camera separation compensation value is obtained.

According to one aspect of the present invention, a method of generating a tolerance database from a nominal database of signals indicative of an image of printed circuit board (PCB) artwork features each having nominal dimensions, the databases comprised of an array of pixels having either a first state (black) or a second state (white), with said black state pixels corresponding to the PCB features, the method including the steps of generating a database having signals corresponding to at least one set of minimum and maximum tolerance values for at least a selected one of the PCB features; providing a minimum database from the nominal and the tolerance value databases such that said selected PCB feature nominal dimensions are reduced by said minimum tolerance value; providing a maximum database from the nominal and the tolerance value databases such that the selected PCB feature nominal dimensions are increased by the maximum tolerance value; comparing the state of each of the pixels in the minimum database with the nominal pixel state and comparing the state of each of the pixels in the maximum database with the nominal pixel state. The method also includes the steps of providing to a tolerance transition database a black state pixel if both of the minimum and maximum pixel states are black; providing to the tolerance transition database a white state pixel if both of the minimum and maximum pixel states are white; providing to the tolerance transition database a black transition state pixel if the minimum and nominal pixels are of different pixel states; and providing to the tolerance transition database a white transition state pixel if the maximum and nominal pixels are of different pixel states.

According to another aspect of the present invention, a system for generating a tolerance database for use in the fabrication of PCB artwork includes an apparatus for generating a nominal database of signals indicative of an image of printed circuit board (PCB) artwork features each having nominal dimensions. The databases are comprised of an array of pixels having either a first state (black) or a second state (white), with the black state pixels corresponding to the PCB features. There is also an apparatus for generating a database having signals corresponding to at least one set of minimum and maximum tolerance values for at least a selected one of the PCB features. An apparatus is included for providing a minimum database from the nominal and the tolerance value databases such that the selected PCB feature nominal dimensions are reduced by the minimum tolerance value. Another apparatus provides a maximum database from the nominal and said tolerance value databases such that the selected PCB feature nominal dimensions are increased by the maximum tolerance value. An apparatus is included for comparing the state of each of the pixels in said minimum database with said nominal pixel state and for comparing the state of each of the pixels in said maximum database with said nominal pixel state. Still another apparatus provides, to a tolerance transition database, a black state pixel if both of the minimum and maximum pixel states are black, while a white state pixel is written to the tolerance transition database if both of said minimum and maximum pixel states are white. There is also an apparatus for providing to the tolerance transition database a black transition state pixel if the minimum and nominal pixels are of different pixel states; and an apparatus for providing to the tolerance transition database a white transition state pixel if the minimum and nominal pixels are of different pixel states. There is also an apparatus for assigning each pixel a numerical weight in accord with its state, for configuring the tolerance transition database into arrays of adjacent pixels, for summing each of the pixel weights in a one of said pixel arrays and for establishing a value of array pixel summed weight as a defect threshold.

According to still another aspect of the present invention, a system provided in accordance with the present invention includes a platen for receiving a substrate; a carriage moveable relative to the substrate and an apparatus for moving the carriage relative to the substrate in response to received signals from a controller. An optical source provides an illumination optical beam and there is an optical subassembly configured with the carriage for directing the illumination optical beam onto the substrate. A camera positioned with the optical subassembly receives a portion of the illumination optical beam reflected from the substrate and provides electrical signal equivalents thereof. A signal processor processes the camera signals into a scan database of pixel signals, with the pixels having either black or white state in accordance with the presence or absence, respectively, of a detected substrate feature. There is an apparatus for assigning each of the scan database pixels a numerical weight in accord with its state; for configuring the scan database into arrays of adjacent pixels; for summing each of the scan database pixel weights in a one of the scan database pixel arrays. The system also includes an apparatus for comparing the scan database array pixel summed weight against the defect threshold value and generating a signal indicative of a defect should the scan database array pixel summed weight exceed the defect threshold value.

According to another aspect of the present invention a system of the foregoing type also includes an adaptive illumination mechanism for maintaining a constant brightness of the illumination beam that has an apparatus for providing brightness control signals to the optical source, for generating a histogram of pixel signal intensities at a reference illumination beam brightness and for determining the total number of pixels in the histogram. There is a threshold computation mechanism for computing the number of histogram pixels which comprise a selected percentage of the maximum pixel signal intensities and a pixel intensity grey scale value above which the maximum pixel signal intensities lie. An apparatus determines the average intensity of the selected percentage of the maximum pixel signal intensities, compares the reference illumination beam brightness with a current illumination beam brightness and computes a brightness correction signal therefrom. Also included is an apparatus for generating a new brightness control signal from the current brightness control signal and the brightness correction signal.

According to another aspect of the present invention a system of the foregoing type also includes an apparatus for providing compensation for defects in the optical subsystem that has a mechanism for creating a pixel database of calibration artwork imaged by the optical subsystem, an apparatus for measuring the relative positions of registration marks in the calibration artwork pixel database; for comparing said measured registration mark relative positions with ideal relative positions and for computing optical defect compensation signals in dependence on the comparison. There is a mechanism for providing compensation for substrate distortion that has an apparatus for identifying in a scan database pixel signals corresponding to registration marks imaged on the substrate and for computing the position of the scanned substrate registration marks relative to one another. There is an apparatus for comparing the computed registration mark relative positions with ideal relative positions and for computing substrate distortion pixel placement compensation signals in dependence on the comparison. The system also has a mechanism for providing compensation for repeatable motion control error that has an apparatus for creating a scanned pixel database of a registration substrate having a sequence of registration marks therein; for measuring the relative positions of the registration marks in the registration substrate; for comparing the measured registration marks relative positions with ideal relative positions and for computing motion control pixel placement compensation signals in dependence on the comparison. Also included is a mechanism for combining the computed motion control compensation signals with the computed optical defect compensation signals with the computed substrate distortion compensation signals, all with the scanned database signals to remove any differences in pixel placement as compared to ideal locations, thereby removing system error.

BRIEF DESCRIPTION OF THE DRAWINGS

FIG. 10 is a simplified illustration of a telecentric lens array used with the system of FIG. 2.

FIG. 11 is a simplified schematic illustration of a system controller 168 used with the AOI system of FIG. 6.

DETAILED DESCRIPTION OF THE PREFERRED EMBODIMENT

Figure 1:
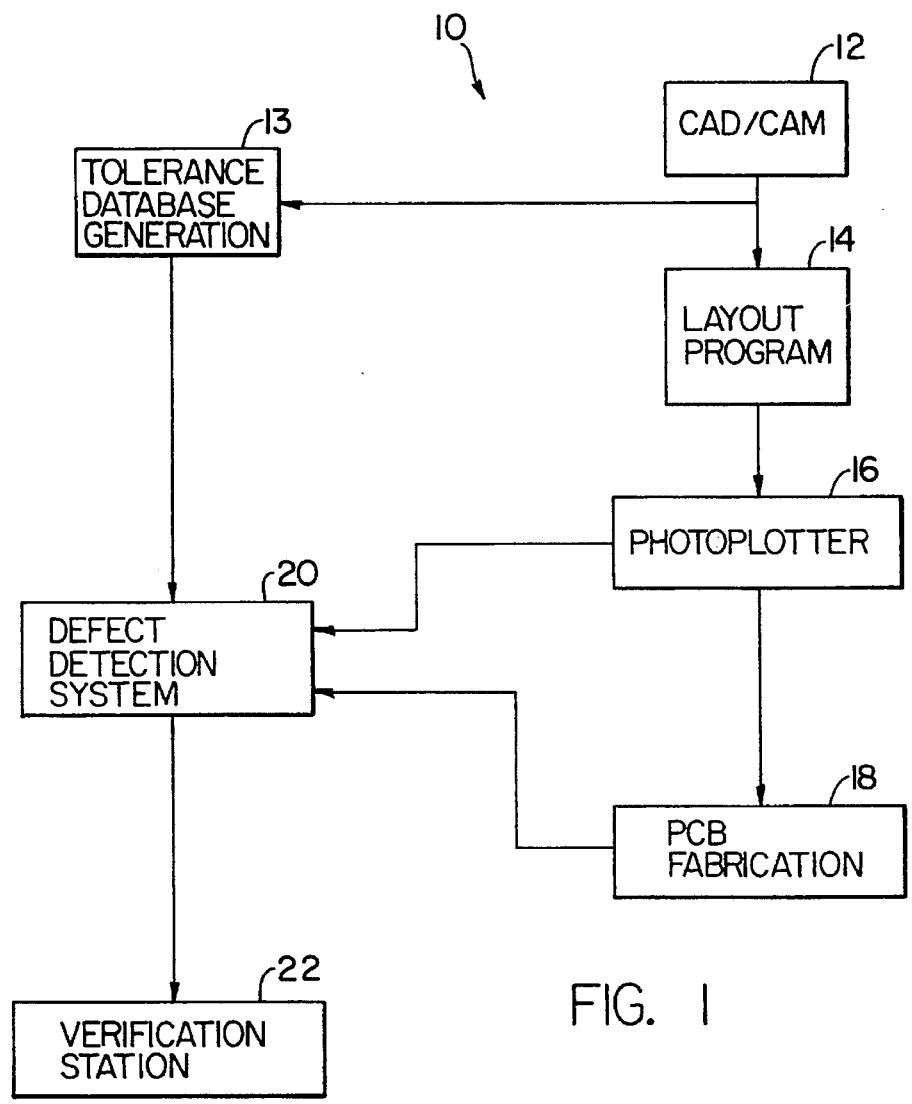
FIG. 1 is a simplified schematic drawing illustrating several devices used in the fabrication of a printed circuit board (PCB).

Referring now to FIG. 1 there is shown in simplified schematic form a series of devices representative of an overall system 10 used in the fabrication of a printed circuit board. Typically, the circuits to be fabricated on the printed circuit board (PCB) are generated using a CAD/CAM apparatus (block 12) which generates a data file containing a schematic of the layout of the PCB circuits. The circuits are configured as geometric features in the CAD/CAM data file. These features are comprised of a series of primitives such as circles, rectangles, etc. Each feature is created from the original CAD data by interpreting the CAD data commands to "flash" or "draw" in conjunction with the CAD data apertures. A "flash" command places an aperture in a single location while a draw command moves an aperture from a start to a stop position filling in along the way. The CAD data is thereby generated in a vector manner.

At block 14 this data file is input to a processor which generates the physical layout for the printed circuit board. The size of the corresponding data file is quite large, so most systems will use one of several known techniques to compress the data. These techniques include a variety of run length encoded (RLE) or equivalent formats. This data file is then provided to a series of devices, including a photoplotter 16 used to fabricate the artwork necessary to make the printed circuit board. The photoplotter is typically a laser direct imager (LDI). The LDI moves the exposing laser beam scanning spot with respect to a write platen and modulates the beam off and on as commanded by the input data. After the line is drawn, the platen is moved by an amount equal to the resolution (i.e. ½ mil.) and the next line is drawn. The process continues until the entire image is exposed on to the film. For a full sized PCB image there will be 52,000 scans each consisting of 40,800 bits, 5000 bytes or 2500, 16 bit words. Lastly, at block 18 the printed circuit board is fabricated using known equipment.

In order to test the printed circuit board for defects, a tolerance version of the CAD data in the form of a compressed data file 13 is also provided to a printed circuit board defect detection system 20, such as the model 1850 defect detection system referenced above. As detailed hereinafter, the model 1850 will decompress the data back to raster format to generate a reference image of the printed circuit board. This image is used with the present system to compare against a scanned image of the printed circuit board to locate defects which can be subsequently be verified at verification station 22.

Figure 2:
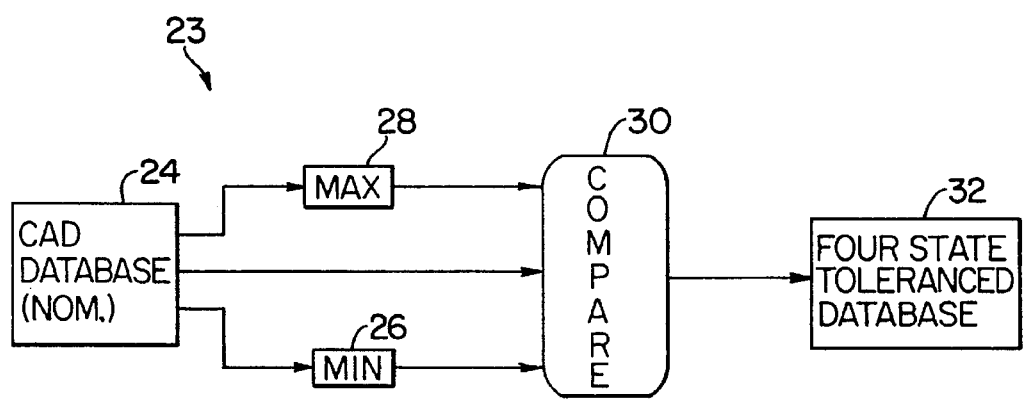
FIG. 2 is a simplified illustration of the operation of a portion of an automatic optical inspection system provided in accordance with the present invention.

Referring now to FIG. 2, there is shown a simplified illustration of the operation of a defect detection system 23 provided according to the present invention. In sum, the system receives CAD data corresponding to the original design of nominally dimensioned PCB features (block 24). Two databases are created therefrom corresponding to PCB features with the maximum and minimum allowable dimensions, respectively (blocks 26, 28). These databases are compared at block 30 and a tolerance, multiple state database is generated at block 32.

Figure 3:
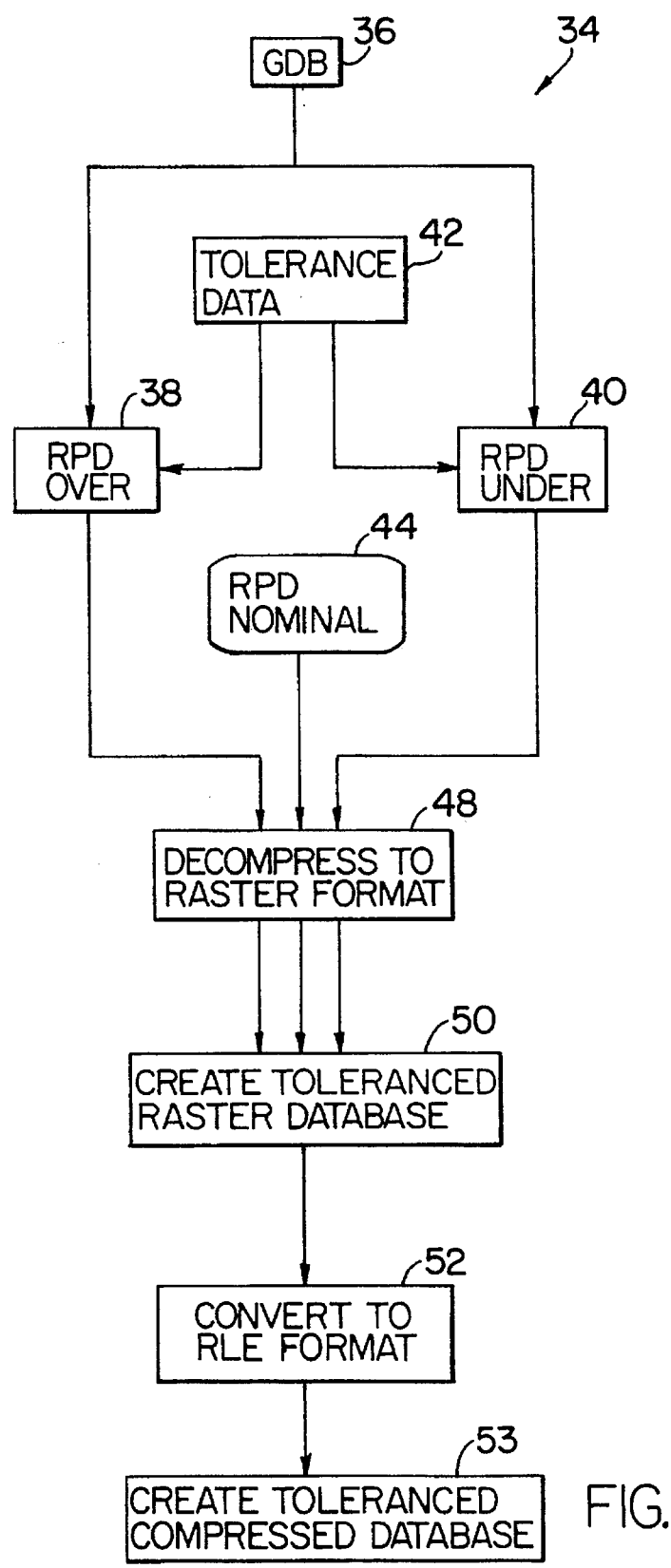
FIG. 3 is a detailed diagrammatic illustration of an algorithm executed by the defect detection system provided in accordance with the present invention.

FIG. 3 is a detailed diagrammatic illustration of an algorithm 34 executed by a portion of the defect detection system 23 used to locate errors in printed circuit board or PCB artwork. In the preferred embodiment, the system generates a transition data base (TDB) having four states (black, black transition, white transition, white) RLE data from two state (black, white) RLE data in a manner detailed hereinafter. Those skilled in the art will note that the present invention can also be practiced with systems where the TDB has three states as well as with systems where the number of states exceeds four.

At block 36, data corresponding to the nominal features on a printed circuit board are provided from a CAD system in a Gerber data base (GDB) equivalent format. The PCB features are represented as geometric primitives, as described hereinabove. Two raster plot databases (RPD) are created at blocks 38, 40 using feature tolerance data provided by a tolerance data file (block 42) in addition to a RPD database 44 containing the nominal features. The present invention provides different tolerances for not only different features, but also for individual examples of specific features, should that be desired.

The tolerance data file contains minimum and maximum tolerance values for the PCB features. The data is then decompressed into a raster form (block 48) for each of the tolerance and nominal values. Most computers lack the capacity to hold a large raster image in main memory. For example, an 18" ×24" PCB image at 0.5 mil resolution requires more than 200 MB of memory. Consequently, the system converts the RLE image to a hybrid raster format in blocks of scan lines in a manner detailed in the '128 patent referenced above. Each block of scan lines is then described by a list of runs and a block of raster data. The data tolerancing apparatus receives at block 50 the hybrid format RLE databases and compares one against the other, pixel by pixel. A new, four state (i.e., color) tolerance raster database is generated from the compared pixels.

Both scanned and database pixels have one of four colors, Black, Black Transition, White Transition, and White. In the tolerance, raster database, assuming positive substrate polarity:

| | | |
|---|---|---|
| Circuitry | = | Black |
| Inner Tolerances | = | Black Transition |
| Outer Tolerances | = | White Transition |
| Background | = | White |

In the scanned data, three thresholds will be applied. First, a median threshold will be applied. Thereafter, thresholds will be applied on either side of the median threshold to characterize "transition pixels". Again, assuming positive polarity:

| | | |
|---|---|---|
| Below Low Threshold | = | Black |
| Between Low/Median Thresholds | = | Black Transition |
| Between Median/High Thresholds | = | White Transition |
| Above High Threshold | = | White |

Thereafter, the tolerance, raster database is recompressed, preferably into RLE format 52 to yield a toleranced, compressed database for use by the system in detecting PCB defects (block 53).

Figure 4:
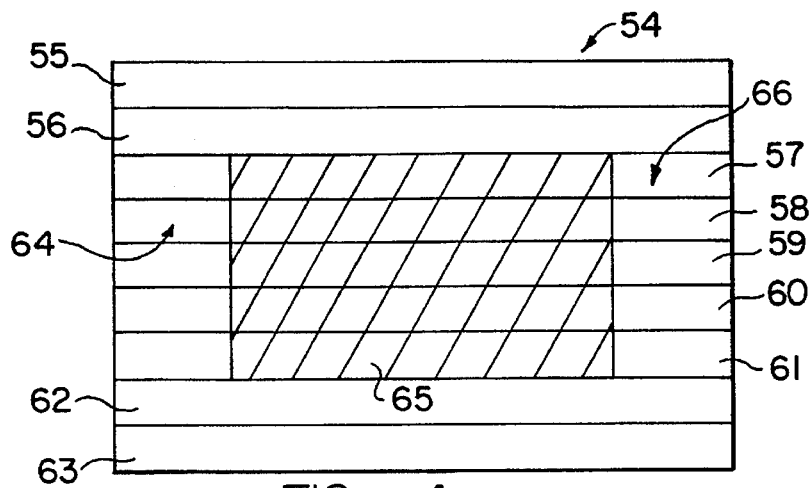
FIG. 4 is a simplified illustration of a sequence of scanlines having a PCB element feature represented as pixels of like color.
Figure 5:
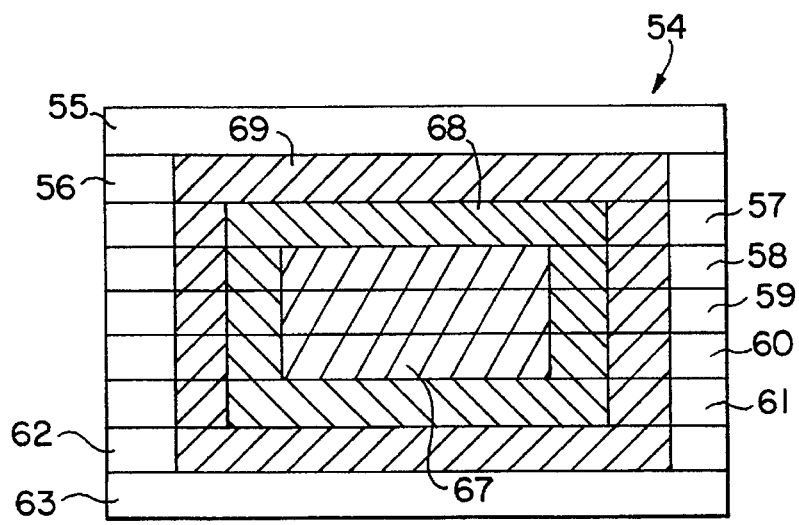
FIG. 5 is an illustration of an image of the PCB feature of FIG. 4 with black, white and transition pixels added.

The effect of this tolerancing process is best seen by way of reference to FIGS. 4 and 5. Referring first to FIG. 4, there is shown a top view of a portion of a PCB artwork feature 54 representing a device on a printed circuit board. Scan lines 55–63 are to be written on the PCB artwork. Each scan line is comprised of a linear array of pixels. Scan line 55 and 56 is outside of the feature and therefore has all "clear" pixels in the Figure or "white" pixels in the data base image. Scan lines 57–61 include the PCB feature and each has white pixels 64 followed by "black" pixels 65 followed by white pixels 66. Scan lines 62, 63 are comprised of all white pixels as they are outside of the PCB feature.

As noted above, the present invention provides for a transitional database wherein PCB artwork features in a reference database are modified to include dimensional tolerances therefor. For the system 23, a global inner/outer feature tolerance can be predefined in magnitude. However, one important departure of the present invention from the prior art is its capability of providing different tolerances for different features.

FIG. 5 contains the PCB feature found in FIG. 4 after processing by the present invention using a preselected value of one pixel for a tolerance. Black pixels represent image areas where the pattern must appear, white pixels represent image areas where the pattern must not appear. At the feature edges are two "grey" pixels which correspond to inner/outer tolerances or acceptable pattern variances. In FIG. 5, region 67 corresponds to that portion of the feature which must appear. Region 68 is a nominal area of that feature while region 69 represents the largest area of which that feature may have. Regions 68 and 69 correspond to the black and white transition regions, respectively.

As noted above, the present invention provides the capability for each feature to be toleranced individually. Therefore, the rectangular feature 54 can be provided with a one pixel tolerance for each transition as shown in FIG. 5, while another feature, for example a circle, can be provided with a greater number of tolerance pixels. Also, each time the feature is repeated in the PCB artwork it may be generated with a user selectable number of tolerance pixels. This feature of the present invention is accomplished by accessing the tolerance data found in a data file (42, FIG. 3) for each feature. In the preferred embodiment, the tolerance data file is accessed during the generation of the oversized and undersized RPD databases. The tolerance value for each feature is expressed as a percent of dimension (X or Y) in look up table form in the preferred embodiment. For example, feature 54 is to be uniformly tolerance by a fixed percentage in both the X and Y dimensions. The preferred algorithm accesses the tolerance data file during the generation of the over and undersized RPD databases. When a feature is encountered during the generation process, the tolerance database is interrogated to see what are the tolerance values therefor. Consequently, that feature's dimensions are altered by the selected percentage(s). The same process is performed for the next (or a subsequent) feature by an amount(s) indicated in the tolerance data file. As stated above, the image is processed in scan line blocks. Those skilled in the art will note that special attention must be paid to the borders between blocks, and that these border conditions are handled in a known manner.

During operation, each scanned pixel will be compared against a database pixel and given a defect weight based on the following table:

| | | DATABASE | | | |
|---|---|---|---|---|---|
| | | B | BT | WT | W |
| S | B | 0 | 0 | 1 | 200 |
| C | | | | | |
| A | BT | 50 | 0 | 0 | 50 |
| N | | | | | |
| N | WT | 50 | 0 | 0 | 50 |
| E | | | | | |
| D | W | 200 | 1 | 0 | 0 |

The weights here are user configurable. Actual weights will be selected to enhance defect detection and minimize "false alarms" where defect signals are generated when scanning acceptable substrates. In order to minimize the volume of data, defect weights are summed within arrays formed by N×N cells or "bins" of pixels. A convolution algorithm is executed by the controller such that a given cell's weight is affected by the weights of its neighbors. A "defect threshold" is applied to determine whether a given cell has a high enough weight to be considered as containing a real defect. Cells that exceed the "defect threshold" will be consolidated with adjacent cells into "real" defects.

With the present invention, there is a consolidation step which follows the comparison of the scan and CAD based data. Pixels are grouped into regions on the substrate surface. In the preferred embodiment the pixels are grouped into 32 by 32 pixel arrays or "bins", with each color given a certain weight. After the consolidation step has been completed, the present system will determine whether the sum of the weights in that particular pixel bin exceeds a certain threshold value indicative of the presence of a defect in that bin. The addition of the consolidation step and the pixel arrangement marks an important point of departure of the present invention over the prior art. In the preferred embodiment, the present system performs the CAD-SCAN data comparison, sums the pixel weights and compares the same against a defect threshold only after RLE forms of the CAD and scan data are available. Those skilled in the art will note that the assignment of weight to each pixel and summation of pixel weights can, in alternative embodiments, be performed at other stages and in other sequences than as set forth with respect to the preferred embodiment.

With the three-state prior art systems, it was conceivable that a short between adjacent features would go undetected if the spacing between the features was less than the width of the tolerance region. This problem is avoided with the present invention. CAD data is compared versus the scanned data to generate a four-color transitional database having two colors of "gray". Unlike prior art systems such as that disclosed in the '128 patent, the tolerance portions of the feature are no longer considered to constitute "don't care" regions where the pixels can either be black or white. Pixel defects in transition areas have a weight associated with them, and thus defects can be found in transition regions.

The present invention provides full raster comparison and a pixel by pixel basis even though the comparison is done in a compressed format. The CAD database relies on a vector feature generation of a type known in the art. Thereafter, the tolerance values for the two additional tolerance colors (light gray and dark gray) are added as described hereinabove. The CAD data is then converted into a run-length encoded format using a vector to raster conversion process wherein the sequence of scan lines are generated in compressed form, preferably a run-length encoded data format.

As a consequence of the above, different features may have different tolerances. A 5 mil line may have a finer tolerance than, for example, a 50 mil line. The difference in tolerances is automatically incorporated into the run-length encoded sequence which, in essence, creates a "sea of pixels". The scan data derived from the substrate is also reduced to run-length format. The present system conducts the comparison between the CAD data and scan data in compressed format, unlike any prior art system which relies on a pixel bit map in a pixel by pixel comparison. The comparison technique of the present invention marks an important point of departure of the present invention over the prior art. The use of compressed data allows for a very fast response and lessens the processor and memory requirements of the present system so much so that the present system can utilize smaller and lower cost workstations and personal computers as opposed to having dedicated hardware required of the prior art.

Those skilled in the art will note that prior art devices manipulated bit map images of the substrate and employed dedicated hardware to accomplish defect detection. In some known systems, video signals from a camera were provided along a video bus to a plurality of cards each of which scanned for a single type of defect such as a line nick, etc. Defect signals were output from the processor cards to the host computer for further processing. These prior art systems are burdened by the need to have hardware and software reconfigured on a per card basis should the design of the substrate change. In order to complete the defect detection process in a reasonable time, prior art systems require large amounts of memory and fast processors found on dedicated hardware since uncompressed video data are processed.

Figure 6:
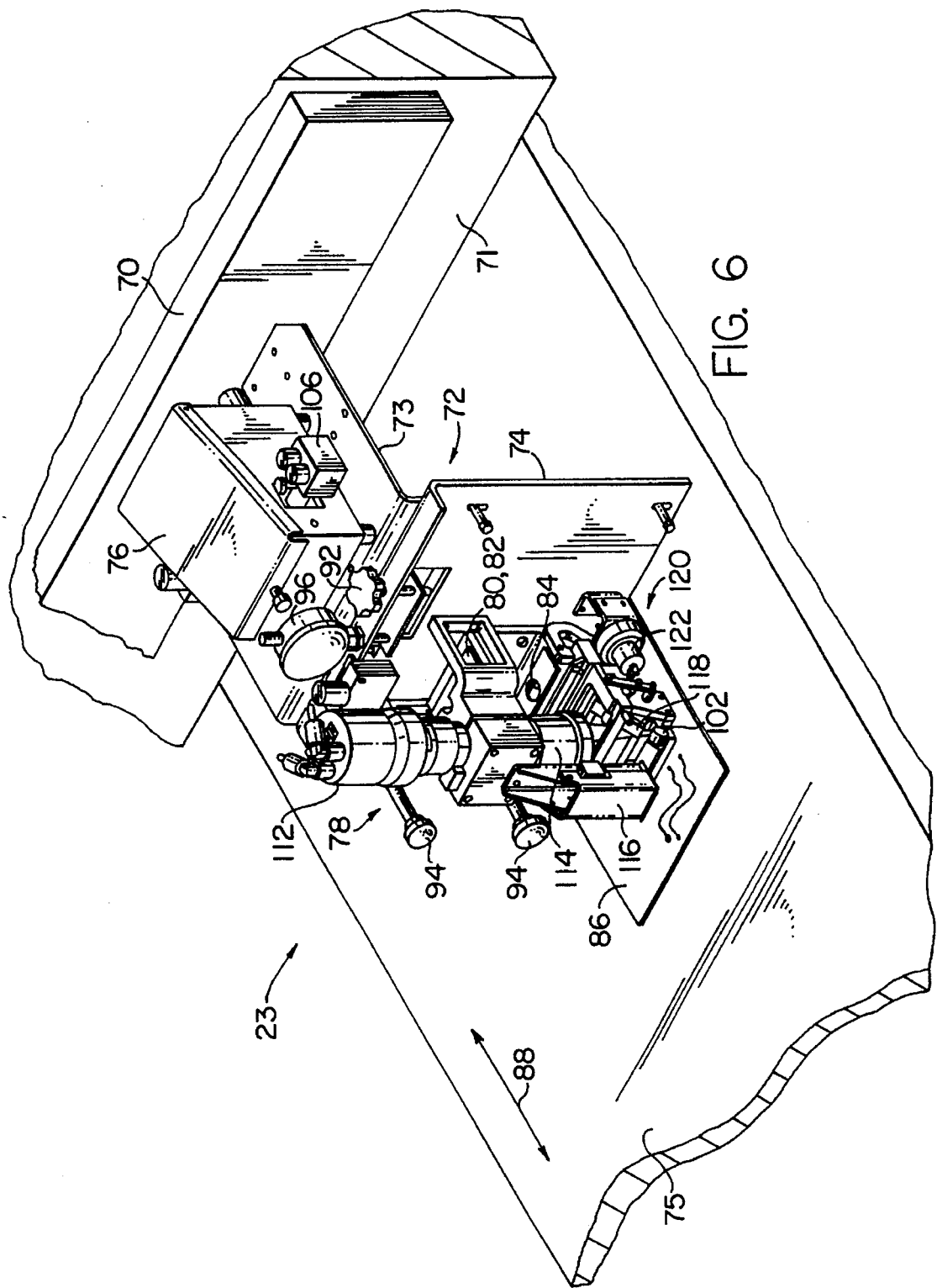
FIG. 6 is a schematic perspective illustration of a portion of an automatic optical inspection system provided in accordance with the present invention.
Figure 7:
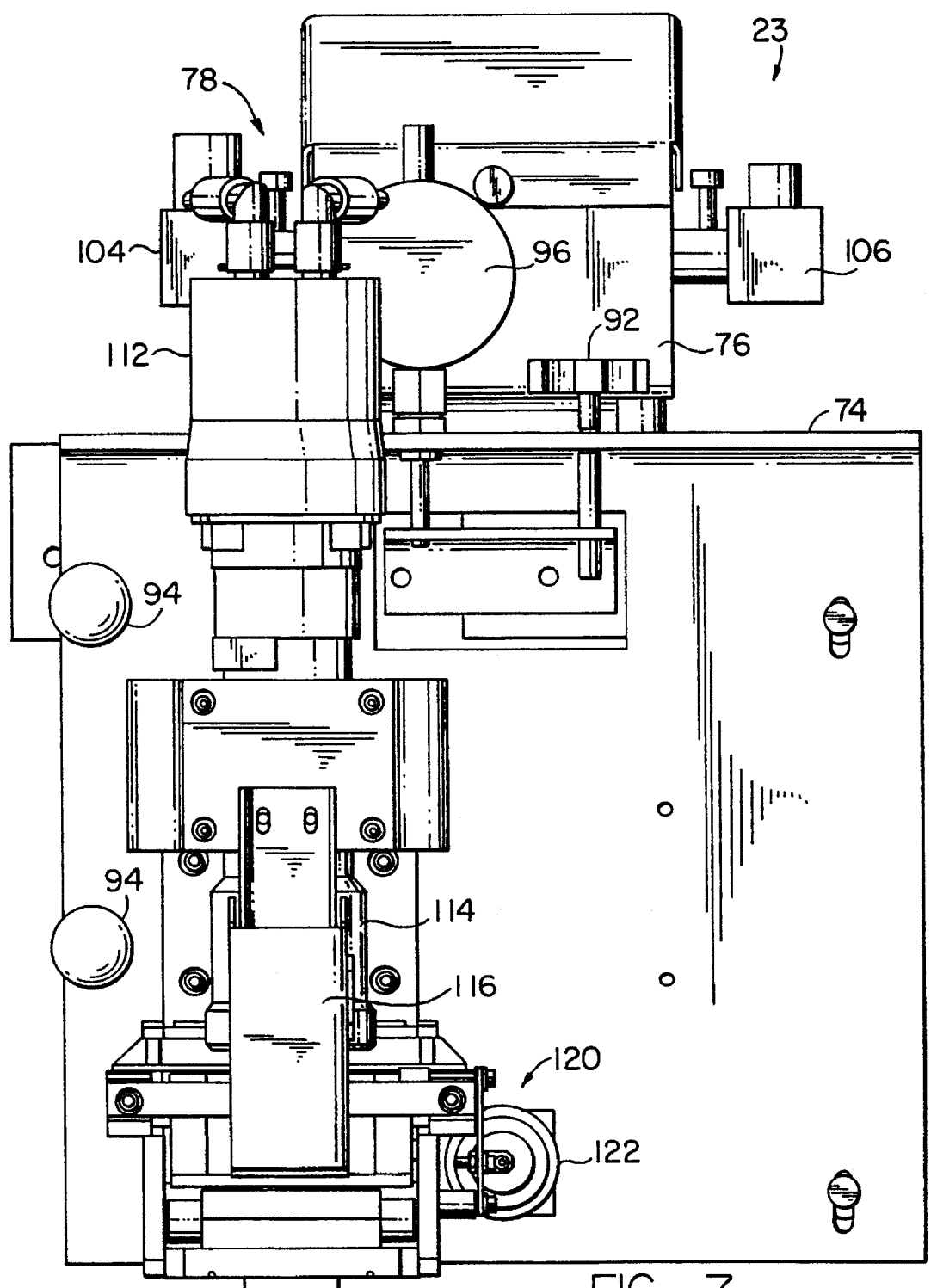
FIG. 7 is a front view of a portion of the system of FIG. 6.

Referring now to FIGS. 6 and 7 there is shown a perspective illustration of a portion of the system 23 provided according to the present invention. There is a transport subsystem in the preferred embodiment that is based on a GSC 44 photoplotter system marketed by the assignee of the present invention. The system comprises a base (not shown) affixed to which is a carriage 70 with a frame 72 having horizontal and vertical elements 73, 74. The carriage moves along a stationary beam 71 over the table. A substrate table 75 moves along steel ways, not shown, perpendicular to the carriage. X/Y servomotors independently control table and carriage positioning. The servomotors are controlled from a system controller (not shown) which receives step pulses from an input/output (I/O) control card associated with the controller. Table and carriage linear encoders provide position feedback to the I/O control card. A joystick interfaces with the I/O control card for table and carriage positioning.

The preferred scan direction is along axis 88, perpendicular to the carriage. Substrate scanning is performed in a serpentine motion. The table and carriage extend to support a 22"×28" inspection area and a 24"×30" substrate size. The table includes a Lenkite pinning system with a combination of fixed pins and sliders. A powerful vacuum system is employed to hold substrate media from 4 mils to 0.25 inches thick.

On top of the horizontal carriage frame surface is a light box assembly 76 which, as described hereinafter, includes dual optical sources. Affixed to the vertical surface of the carriage frame is an optical subassembly 78 comprised of a plurality of Fresnel lenses 80, 82 and aperture 84 more clearly visible in FIGS. 8, 9 for illuminating a substrate 86 located on the platen or table. The vertical element has slots that receive height clamps 94 which control the displacement of the optical subassembly relative to the substrate accomplished by turning height adjustment mechanism 92. The actual displacement is indicated on dial gauge 96 in the preferred embodiment. Those skilled in the art will recognize that other configurations can be equivalently substituted.

Figure 8:
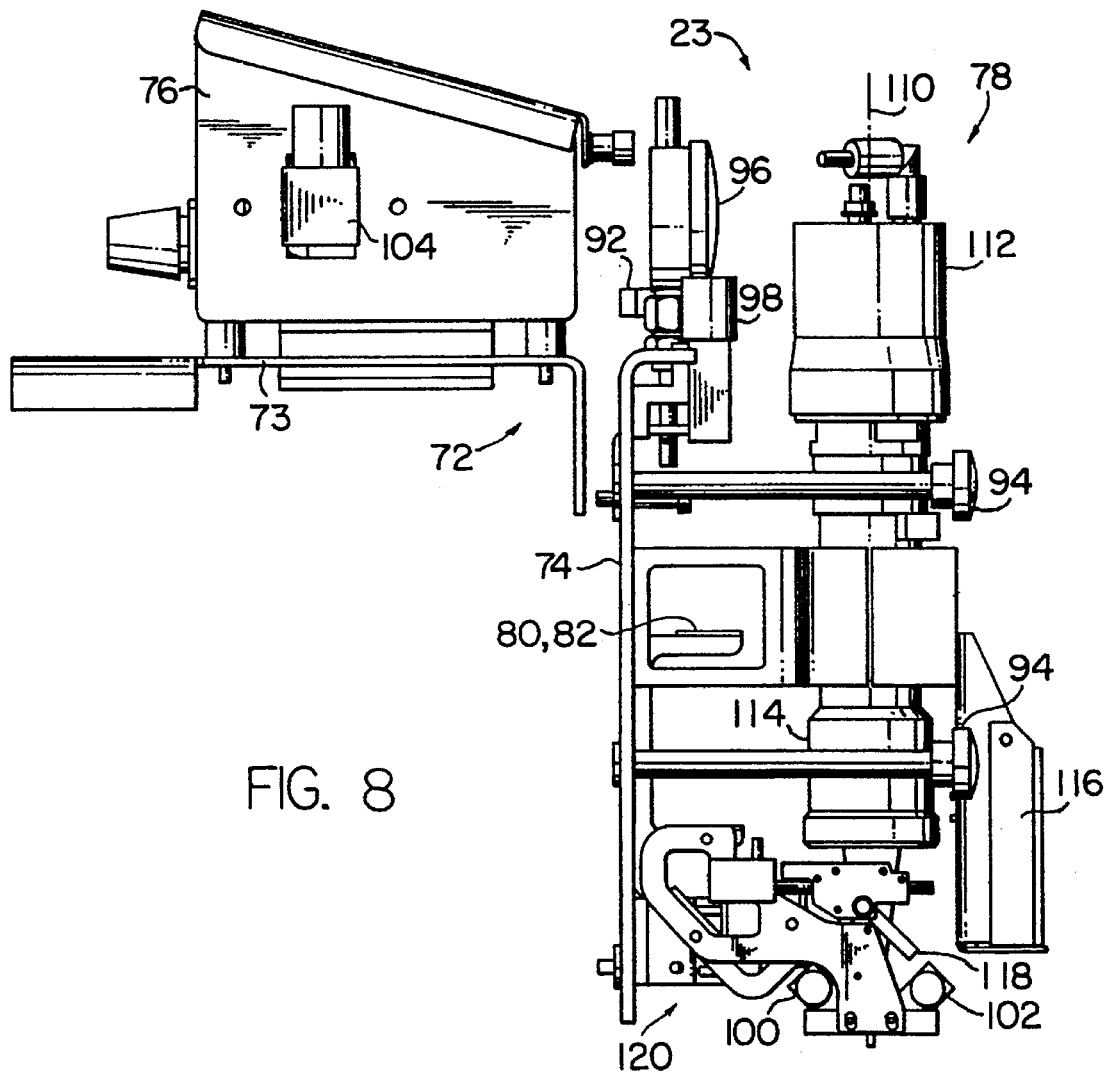
FIG. 8 is a first elevational view of the system of FIG. 6.
Figure 9:
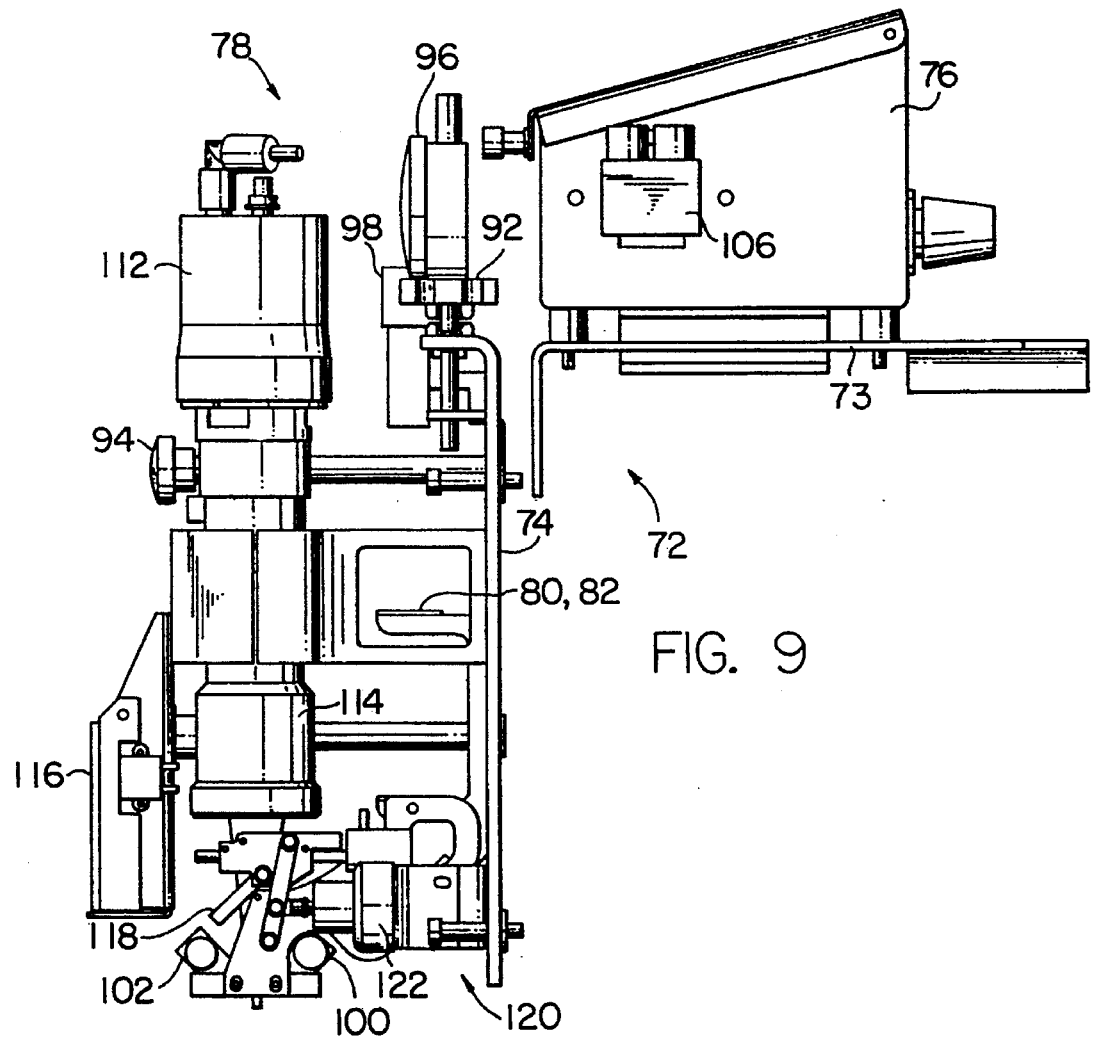
FIG. 9 is a second elevational view of the system of FIG. 6.

FIGS. 8 and 9 show left and right side elevational views of the system 23. The light box assembly contains two separate optical sources, preferably halogen bulbs that are not shown. One bulb provides diffuse illumination for those substrates like film which require the same, while the other provides specular illumination for highly reflective substrates like copper. Each optical source presents its light to specular 98 and diffuse fiber optic heads 100, 102 by way of separate optical fiber couplers 104, 106. The Fresnel lenses are adapted to collimate light before final presentation to the substrate.

An optic axis 110 defines the path along which light travels to the substrate when operated in a specular illumination mode and from the substrate in both the diffuse and specular illumination modes. Along the optic axis there is a camera 112 which receives reflected light from the surface that passes through Fresnel lens 82 and scan lens 114. Specular illumination along the optic axis is provided through the specular fiber optic coupler which, in the preferred embodiment, is configured with the camera which is preferably a Loral Fairchild Model 15005.

There is also a light pointer assembly 116 mounted to the optical exposure head and displaced a preselected distance from both the substrate and the intersection of the optic axis with the substrate surface. The light pointer assembly contains an LED or other light source which is used to illuminate a portion of the substrate during the registration and initialization process in a manner detailed hereinafter. An ink-marker mechanism (not shown) may also be mounted on the optical head as well. The I/O control card would control the operation thereof through a 1-bit output port. A pellicle 118 is used as a beam splitter for those applications where the reflected and illuminating beams must be split. The pellicle is moveably affixed to a pellicle removal assembly 120 that includes solenoid 122.

Scan lens 114 is preferably a telecentric lens assembly. As is well known in the art, a telecentric lens is one in which the aperture stop is located at the front focus, resulting in the chief rays being parallel to the optical axis in image space, or the exit pupil is at infinity. The telecentric lens assembly is provided in the present invention to ensure that variations in thickness in the substrate region under analysis do not result in variations in focus. An example of the preferred telecentric lens assembly 142 is shown with respect to FIG. 10. Shown therein are lenses 144–150 which are ground to ensure that rays 152 which emanate from points 154, 156 on object 158 which are displaced from an optic axis 160 intersect the plane of image 162 at the same angle 164 regardless of the displacement 166 from the optic axis.

FIG. 11 is a simplified schematic illustration of a system controller 168 used with the AOI system of FIG. 6. A host computer 170 communicates with a central processing unit (CPU) 172 via an RS 232 standard serial connection (line 174). The CPU, preferably an Intel brand 80386 or subsequent generation processor, communicates via a conventional AT signal bus 176 with other electrical components associated with the controller. These include a power supply 178 as well as a data encoder and memory 180. The data encoder and memory also communicate via a small computer systems interface (SCSI) data channel 182 with the host computer. A line scan processor 184 is also included with the system controller which communicates with the other electrical components along the AT bus as well as with the data encoder and memory via a direct DMA connection 186. The line scan processor acts as a camera controller. Output is controlled by a I/O controller 187 whose outputs include a scan synchronization signal on line 188 to the data encoder and memory as well as control signals to the ink-mark driver 189 and lamp controller 190. Input signals to the I/O controller are received from a servo controller 192 and a joystick driver 194.

The lamp controller, as detailed hereinafter, receives signals from a power supply 196 to provide voltage signals to the lamp and also receives control signals from the I/O controller to maintain a pre-established level of illumination. The line scan processor also receives signals from a CCD camera 197 powered via signals from power supply 199. The servo controller powered by power supply 201 sends and receives signals to and from X and Y servo units, 198, 200 which are conventional and known in the art to provide for the X & Y movement along the table surface. The output signals from the data encoder which comprises scan data are received on line 182. Output signals from the present AOI system are presented along an Ethernet network to be received by both the CAM and verification stations. Signals from the CAM station can also be presented to the plotter to plot out the image of the inspected board.

As noted above, the present system is also characterized by an adaptive illumination system. The purpose of adaptive illumination is to compensate for process variations such as differences in substrate reflectivity as well as any change in the illumination due to bulb degradation. The voltage applied to the lamp is controlled by the inspection system to maintain a preset illumination. The adaptive illumination system is designed to maintain a constant signal brightness level as seen by the line scan camera.

Figure 12:
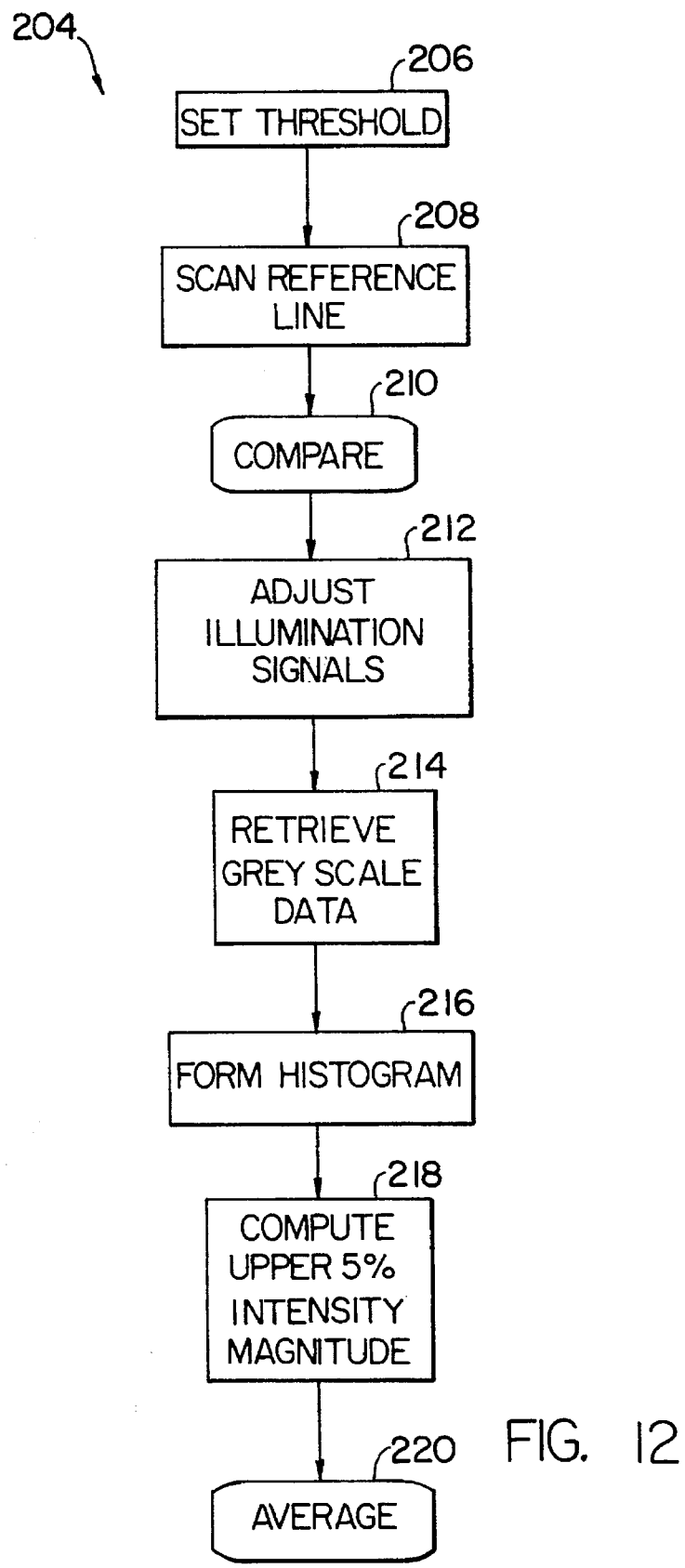
FIG. 12 is a diagrammatic illustration showing the operation of an algorithm executed by the adaptive illumination apparatus provided by the present invention.

A diagrammatic illustration of an algorithm 204 executed by the adaptive illumination system is seen in FIG. 12. When the threshold levels are set (box 206), a reference line scan of the gray scale data is taken at box 208. The thresholds are relative to this initial condition. Both prior to an inspection operation as well as during the inspection process, gray scale data is obtained and compared against the reference data (box 210). The illumination is adjusted to zero out any difference between the two at box 212. This adapts the signal relative to the fixed thresholds and is equivalent to adapting the thresholds for a changing signal, except that the illumination adaptation maintains better use of the line scan acquisition board's A/D dynamic signal range. The illumination adaptation also simplifies the hardware design in that the thresholds do not have to be adjusted during the scanning process.

For both the initial and subsequent inspection scans, grey scale data from one or more line scans is retrieved (box 214). A histogram of this data is formed at box 216. That is, 256 histogram bins are accumulated to characterize the intensity distribution. The objective is to determine the brightest part of the signal (e.g. direct reflection from copper) while remaining unaffected by normal variability. The highest 5 percent of the histogram is found (box 218) and the numerical average of this part of the histogram is determined (box 220). This value is used to represent the current illumination/reflection characteristic.

It has been found that the illumination and/or camera response is not linear, so a static calculation of a new illumination setting is, therefore, not sufficiently accurate. Repeated applications of this calculation have resulted in oscillations in the illumination. As a result, a simple proportional closed loop feedback control using iterative setting of the illumination is implemented in the preferred embodiment and provides consistent compensation. Good results are obtained with changes in material (reflectivity) as well as changes in illumination set points. The present system consistently returns the illumination to the correct nominal level as required for use with a fixed threshold.

In operation, an illuminated "sample" is formed by accumulating an intensity histogram over many scan lines. The accumulation over multiple scan lines avoids the possibility of adjusting the illumination based on a single scan viewing a dark region on a substrate. In the preferred embodiment, data is accumulated from multiple readings of the flow of gray scale data in a "z" pattern, or over a set of multiple scan lines. The histogram is analyzed as follows:

1) The histogram values are summed to determine the total number of pixels over which the histogram was accumulated.

2) A threshold is computed which corresponds to the number of pixels which make up the top 5 percent of the histogram, i.e., threshold=(int)(fraction * (double)n);

where fraction is 0.05 and n is the sum of all histogram bins compared in step 1.

3) The gray scale value above which the top 5 percent of the intensity values exist is then found and the average intensity above this point is computed (max_average). As an example:

```
cumm = 0;
avg = 0;
for (i = 225, i >= 0; --i)
    {
    cumm += hist[i];
    avg += (long)hist[i] * (long)i;
    if (cumm >= threshold)
        break;
    }
max_average = (int) (avg/(long)cumm);
``` where "cumm" is the grey scale value and "avg" is the average intensity.

Figure 14:
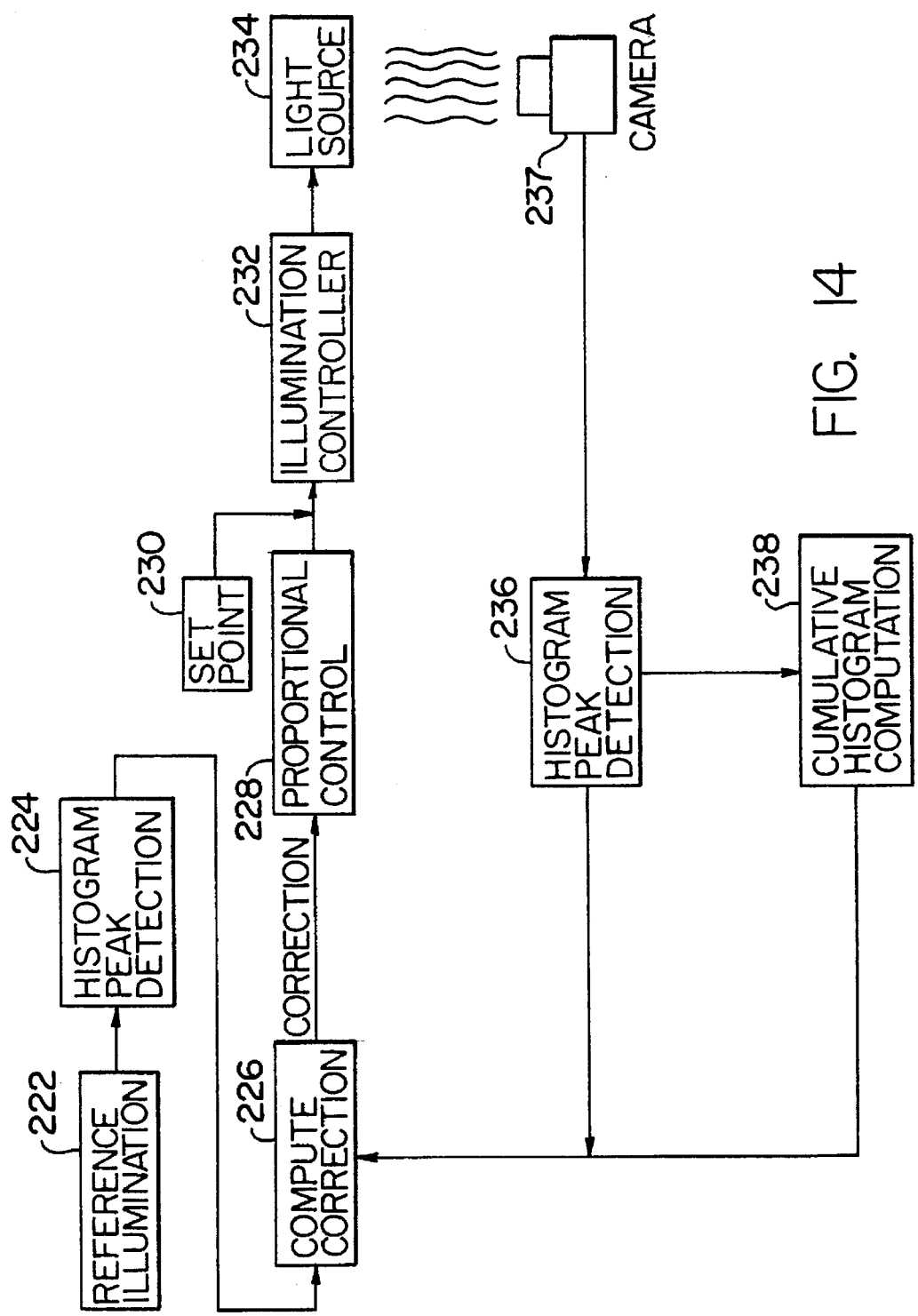
FIG. 14 is a diagrammatic illustration of an illumination beam control algorithm executed by the systems of FIG. 6.

The above calculation is performed for both the reference condition as well as during the inspection operation. These averages of the top 5 percent of the intensity are used in the closed loop computations detailed in FIG. 14. At box 222, reference illumination is set and the histogram peak is determined (box 224). A correction is computed (box 226) in which a ratio of reference signal to current signal is calculated. Proportional control signals for the lamp power supply are generated (box 228). The set point for the lamp is adjust at box 230 and the corresponding lamp control signals are generated (box 232) for presentation to the light source (lamp) at box 234. Feedback from the camera 237 in the form of a subsequent peak detection (box 236) is determined thereafter. The "histogram peak detection" steps in FIG. 14 represent the computations outlined above. The "proportional control" block forms a new light setting as follows:

$$1_{t+1} = K * \text{correction} * 1_t + (1-K) * 1_t$$

where "$1_t$" corresponding to the current brightness control signal value at time t, "correction corresponds to the value of the brightness correction signal and "K" is an empirically determined constant. Control signal loop closure is accomplished over a sequence of reference scans. For each group of reference scans, a cumulative histogram is formed (box 238) and then applied according to the above closed loop algorithm.

As noted above, the present system is a production tool for inspecting phototools and inner/outer Printed Wiring Board (PWB) layers at critical manufacturing stages. The system utilizes CAD signals as a basis for inspection. Data acquired from a scanned panel is directly compared against the CAD data used to create the original phototool. In addition, scan data is "rubber sheeted" or compensated with respect to the inspection database to account for global distortion and misregistration of the panel under test. The distortion compensation will facilitate a direct pixel to pixel comparison and is accomplished in a manner set forth in U.S. Pat. Nos. 4,783,826 and 4,859,999, incorporated herein by reference. Regional pixel comparison differences are consolidated into defects and reported to the operator.

The primary design goals realized by the present system are to provide an intuitive, fully functional system while minimizing recurring cost. Throughput is an important but secondary goal. The system in the preferred embodiment offers moderate throughput at a low cost. As compared to known systems, a system provided in accordance with the present invention inspects a PCB substrate more slowly (approximately 0.75 times as fast) than a known system but does so for one third the cost. Increased throughput can also be achieved by extending processing power of the front end with faster hardware and/or parallel processing. An optional second camera and data channel can be configured for additional parallel processing.

Exemplary hardware used in the preferred embodiment is set forth hereinafter. The "front end" componentry consists of an inspection station and optional inspection co-processors. In a 2-camera system an inspection co-processor is standard. The inspection station is the central communications point for the rest of the components set forth with respect to FIG. 1. It interacts directly with the user interface. Included with the inspection station hardware but not specifically shown in the figures are a workstation, high resolution monitor, keyboard, mouse, hard disk, network connection, and off-line storage options, all schematically illustrated by computer 170 in FIG. 11. The computer may be a high end PC or low or high end RISC workstation. In addition, for increased job throughput, the Inspection Station can be two physical workstations. Job Setup could be done on one station while panel inspections are performed on the other.

The workstation includes a hard disk for on-line storage of the Gerber AOI system programs and environment, job files, and defect files. An Ethernet interface is provided for network connection to the CAM Station, off-line verification station, etc. An optional 4 mm DAT tape drive is offered for off-line file storage. The inspection station has an RS-232 serial connection for command/control signals and has a second SCSI bus for up-loading of scan data from the data encoder card. To reduce SCSI bus traffic during up-loading, the primary SCSI bus is used for the disk and tape drives. Optional inspection coprocessors can be networked to the inspection station for parallel inspection processing. In an alternative 2-camera system, the camera/lens subsystem, illumination/projection subsystem, line scan processor, and data encoder is duplicated for a second data channel.

A Loral Fairchild Model 15005 line scan camera is preferred and comprises a 2048 element CCD camera with a 13 micron pitch. It has a maximum video rate of 20 MHz and a maximum scan rate of 9700 lines/sec. The camera has an associated linear power supply to provide +−12 V and +5 V DC power. All camera control signals are supplied by the line scan processor. In alternative embodiments a set of illumination "stops" is provided to control the angle of incidence of light onto the panel. These "stops" produce specular, diffuse, or combined specular/diffuse illumination as needed. A set of spectral filters and polarizers are provided to improve image contrast for some substrate materials. The system operator manually positions these items along the optic axis when appropriate. Lamp intensity is modulated in accordance with the algorithms detailed herein. This regulator card will accept voltage values from the I/O controller via an 8-bit input port.

As noted above, an Intel 80386-based CPU controls the operation of the data encoder, line scan processor, and I/O controller. The CPU communicates with other system controller components via the ISA (PC-AT) Bus in a passive backplane configuration. A multi-tasking operating system kernel and embedded control software resides with the CPU. The data translation (DT-2856) line scan processor is employed and provides complete control over the line scan camera operation. The DT-2856 processor accepts analog video data from the camera, digitizes, and outputs 8-bit/pixel grey data over a DT/Connect port to the data encoder and performs camera offset/gain correction and line-to-line DC adjustment to compensate for camera thermal drift. All operations are performed in real-time at speeds up to 20 MHz.

The data encoder processor thresholds and compresses scan data and outputs the same to the inspection station at up to 20 MHz. Scan synchronization signals are input from the I/O Control card. The card will accept 8-bit/pixel grey data from the line scan processor via a high speed video bus. Scan data in the preferred embodiment is passed through a distortion look-uptable (LUT) to compensate for optical distortion and to translate pixel sizes from 13 microns to 0.5 mil. Optional 0.25 mil data can be produced by sub-sampling 0.5 mil pixels along a scan line.

The line scan processor operates in grey level mode or threshold mode. In grey level mode, 8-bit/pixel scan data signals are passed to the inspection station without being thresholded. In the threshold mode, scan data is passed through a threshold look up table (LUT) to produce 3-bit/pixel thresholded data which is then compressed using a run length encoding scheme. Each "run" of pixels is represented by a 16-bit word, with 13 bits for position and 3 bits for color. Data is buffered up in DRAM that physically resides on a daughter card (not shown) that has a 32 MB minimum configuration and expansion capabilities. Data is transferred to the inspection station in blocks via a SCSI bus. A dual ported, FIFO mode memory architecture transfers the data as soon as memory blocks are full.

Software residing in the CPU supplies the data encoder with setup data, LUTs, and run-time SCSI control. To support adaptive illumination control, the data encoder stores the grey value of periodic pixels in a register available to the CPU on the PC-AT Bus.

A GAT-2 card, marketed by the assignee of the present invention, is the preferred I/O controller. This card controls substrate table and carriage motion as well as joystick operation, lamp intensity, and ink-marker operation. The card supplies step pulses to the GTP-310 servo card for table/carriage positioning. It receives position feedback signals from the GTP-310 and provides scan synchronization signals to the data encoder and line scan processor. Input sensors monitor limit and home conditions and joystick movement. An 8-bit output port interfaces to the GTP-367 voltage regulator card. A 1-bit output port controls ink-marker operation.

Software for front end componentry is written in C++ and ANSI-C programming language. The operating systems are UNIX based. The graphical user interfaces (GUIs) are X-Windows based and have a Motif look-and-feel. There is a GUI-based program for the initial job setup in which an operator inputs CAD and drill data for a job, as well as for other functions such as panelize, inspection parameter entry, and inspection database generation initiation. The present system uses known Gerber Plotter Control (GPC) software to provide the CAD data input and panelization functions that is enhanced with additional functions for AOI and is referred to in the preferred embodiment by the trademark "Gerber Inspection Control" (GIC) software. The enhanced software of the present invention provides parameter entry for aperture tolerances, finished holes sizes and tolerances, registration points, inspection region, and don't inspect regions. It will also accept drill data as input signals and initiates generation of the inspection database.

A background program generates the inspection database. GIC controls the generation of the inspection database and provides panel layout information, aperture tolerances, etc. Another algorithm associated with the system controller automatically identifies registration points in the CAD data and searches therethrough for appropriate points to be used for "rubber sheeting" compensation detailed herein.

The present system also includes a second GUI-based algorithm for performing inspection related operations and inkmarking and utilities for file management, hardware calibration, etc. This algorithm can be initiated by the operator via a button in GIC, analogous to the similar GUI schemes for plotter control in other systems. Operating in the background in the system controller are algorithms for command/control of the various functions, including a protocol for communications over an RS-232 serial connection.

A "comparison" program resides in the present system and each inspection co-processor for comparing inspection database files with scanned image files and generating a substrate defect list. A "scheduler" program is included for schedule comparison of the previously scanned substrate region or stripe on an available processor. A multi-tasking operating system kernel and embedded control software also reside in the CPU. The software and operating system can be stored in ROM or down-loaded into RAM, depending on the application and component selection. The preferred kernel is DOS-compatible.

Other system controller software includes setup data and LUTs as well as run-time SCSI control for scan data transfer. Other system controller software supplies the I/O control card with requests for table/carriage movement, lamp voltage changes, and ink-marker activation. Table/carriage position and joystick operation are also monitored as detailed with respect to FIG. 12. The scan line processor will periodically transfer scan data signals from an associated data register to the data encoder, analyze signal intensity, and modulate the lamp voltage accordingly.

The following constitute the basic steps performed by an operator during an inspection. CAD and drill files for the substrate (e.g., panel) are imported from the CAM station. If the CAM Station is running GPC, setup files, aperture files, etc. are also imported via magnetic tape, floppy disc or using TCP/IP over an Ethernet network. The operator creates aperture tables for each CAD and drill file used for the panel. The drill file aperture table will contain finished hole sizes rather than tool sizes. The operator creates tolerance tables for each aperture and for each finished hole size used in the CAD and drill files for the panel. An inner and outer tolerance is entered for each. The operator enters these values directly in the GIC GUI, similar to current aperture table entry in GPC software. In addition, the tables can be created automatically based on preset aperture size vs. tolerance rules.

The operator loads the CAD and drill Files that comprise the panel into the GIC software workspace. If GPC was used at the CAM station and a Setup file was created, this file is read instead to automatically set up the panel. The panel layout is specified using GIC software's panelization functions. This organizes the CAD and drill file data to precisely represent the panel to be inspected. Thereafter, the operator uses a "rubber-band box" command to identify the region of the panel to be inspected. The same technique is used to identify optional "don't inspect regions" within the inspection region. These don't inspect regions are typically used to eliminate inspection of lettering, coupons, etc. that are non-functional in the circuit.

Three registration points are identified in the panel corners to be used for placement and distortion correction during inspection. Three modes of operation of the present system are provided in the preferred embodiment. The first allows for these points to be chosen automatically during database generation. The second provides for the operator to explicitly define the points by manual selection in the GUI. The third option is for the operator to include a registration point template with a panel definition. In order to use the third option, the operator will have created several templates (e.g. one for each standard panel size) that include predefined registration points. With this option, the operator places inspection registration markings outside the circuitry that conform to registration point requirements. This background task will be initiated following operator entry of setup parameters. The CAD and drill data is converted to a tolerance database for inspection. If the operator selected "auto-finding" for registration points, these points are identified here.

The following basic steps are used to inspect a set of panel substrates for the same job. Initially, the operator selects a job inspection data base from the list of available ones and sets the parameters necessary for inspection of the current panel lot (e.g. panel material type, polarity, ink-mark on/off, pinning on/off). The first panel of the lot is placed on the table and the operator uses the joystick to jog the table so that the light pointer is over the first registration point identified in the database. The initial light level will automatically be set just below saturation. The operator sets the inspection threshold using a mouse-driven, interactive tool. This tool displays the effects of different thresholds on a view of the canned image. The light level can be changed "on the fly" during the inspection scan if the image intensity characteristics vary greatly. The system determines the precise panel placement by correlating the scanned first registration point vs. the registration point area identified in the database. Generally this step will only be performed on the first substrate in a lot. For the case where substrates aren't pinned and panel positioning isn't consistent, the operator will locate the first registration point for each panel.

Thereafter, the system automatically scans the other registration points and performs the same correlation to determine "rubber sheeting" compensation values in the manner set forth herein. The system scans the panel and up-loads the scanned image to the inspection station, a stripe at a time. The inspection comparison will be performed at the inspection station (or inspection co-processors) as the stripe data are received. Defect locations will be consolidated and stored in a file on disk. If ink-marking has been selected, the table jogs to each defect and places an ink mark at the defect. The operator unloads the panel. If off-line verification is needed, the panel will be brought to the verification station.

The primary data sets produced in the present system are the inspection database, scan data, and defect data. Each substrate to be inspected will have an associated inspection database. The same original CAD data and rendering software is used for both the plotter database and the inspection database. Drill data used for the inspection database is the same data used to control the drilling machine to insure accuracy of the inspection database.

The inspection database is created by the system controller during setup as a Run Lengh Encoded representation of the panel to be inspected. Circuitry areas, background areas, and tolerance bands are represented by different colors. An individual database file is created on disk for each 1" wide stripe of panel data. The data encoder thresholds and compresses camera scan signals and up-loads the same to the inspection station via the SCSI bus. Like the inspection database, scan data is run length encoded. Circuitry areas, background areas, and transition areas are represented by different colors. Scan data for each wide substrate stripe are treated as separate entities. During the inspection comparison, "defects" are identified. Each defect will have an associated location, type and size. A defect file is created on the hard disk for each inspected panel. This file contains job header information and the list of defects. It is used for on-line verification, or transferred to an off-line verification station.

As noted above, each scanned image is "rubber sheeted" to the corresponding inspection database so that a precise pixel to pixel comparison can be performed. When an inspection database is created, additional database lines are created for a small region around each registration point. Prior to each panel inspection the system scans each registration point in succession. Thresholded, compressed camera data for each registration point region is up-loaded to the Inspection Station via the SCSI signal bus.

The present system also comprises a correlation algorithm to search for the database registration point within the scanned region. The scanned region is larger than the database region. The two-dimensional images are projected both vertically and horizontally so that one dimensional correlations can be performed to achieve higher throughput. The horizontal and vertical CAD projections are compared against their scanned counterparts to produce a "best fit".

This general purpose program will work with any sufficiently isolated and well defined registration point configuration. The X/Y offsets between the database and scanned registration points are used to compute "rubber sheeting" compensation values.

Three registration points are required to account for panel translation, rotation, and global stretch/shrink. The image scan start/end positions are modified to account for translation error. The table/carriage movement is modified to scan stripes along a slope to account for rotation. The stripe start positions are adjusted to account for stretch/shrink in the X direction, while scan lines are duplicated/skipped to account for stretch/shrink in the Y direction.

The preferred embodiment is characterized by resolutions of 0.5 mil (2000 dpi) and 0.25 mil (4000 dpi). The Data Encoder also provides for creating a sub-sample of the 0.5 mil pixels along a scan line to achieve 0.25 mil pixels, thereby doubling the resolution. The 8-bit grey values of adjacent 0.5 mil pixels are averaged to compute an 8-bit grey value for each subsampled 0.25 mil pixel. The present invention is also characterized by a pixel interpretation apparatus which allows for subsampling yielding 4,000 dot per inch resolution from a 2,000 dot per inch camera by interpolating adjacent pixel values. As is known, features on a substrate transit from a single state black or white to an opposite state in a discreet quantum manner. However, as recorded by a camera there is a Gaussian distribution of intensity over adjacent pixels on the edge of a feature. The present four-color preferred system employs an apparatus since because of lens diffraction effects an edge produces a transition across several pixels for averaging adjacent pixel values to create an intermediate pixel effectively providing eight colors and yielding a doubling in resolution. Set forth below are examples.

| | |
|---|---|
| Inspected Materials | Artwork |
| | Diazo |
| | Silver Halide |
| | Inner Layers |
| | Bare Copper |
| | Developed Photoresist over Copper |
| | Outer Layers |
| | Bare Copper |
| | Bare Copper w/Holes |
| Inspection Resolution | 0.5 mil or 0.25 mil, Selectable Per Inspection |
| # of Cameras | 1 or 2, Configurable at Factory |
| Max Media Size | 24" × 30" |
| Max Inspection Size | 22" × 28" |
| Panel Thickness Range | 0.004"–0.250" |
| Min. Capturable Defect Size | 0.5 mil (@ 0.25 mil Resolution) |
| | 1.0 mil (@ 0.5 mil Resolution) |
| Inspection Time (18" × 24") | <3.0 min (1 Camera, 2000 dpi) |
| | <2.0 min (2 Cameras, 2000 dpi) |
| | <5.0 min (1 Camera, 4000 dpi) |
| | <3.0 min (2 Cameras, 4000 dpi) |

The present invention also encompasses embodiments which have more than one scan camera. Prior automated optical inspection systems, i.e., those for printed circuit boards, have used multiple scanning cameras, but these systems have required extreme care in the mounting and alignment of the cameras to avoid either overlapping the scan bands or leaving gaps between adjacent bands. The present invention eliminates the need for the careful alignment of the scanning cameras.

Figure 13:
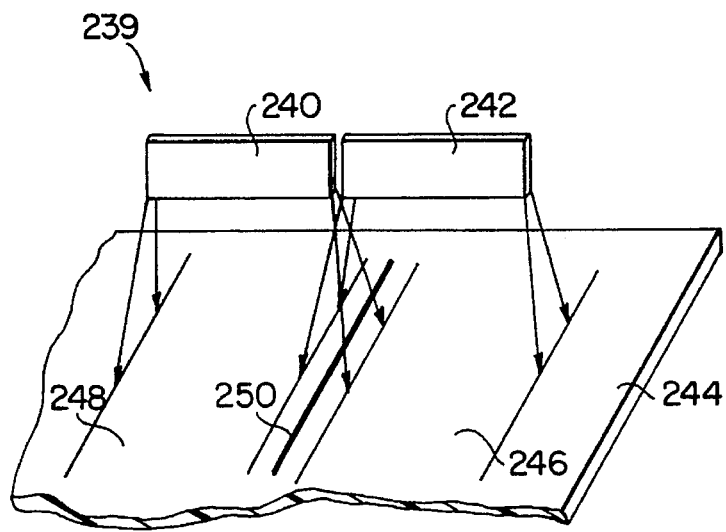
FIG. 13 is a simplified illustration of a portion of an alternative embodiment of an automatic optical inspection system provided according to the present invention.

In FIG. 13 there is shown a portion of an automatic optical inspection system 239 characterized by multiple cameras. Illustrated therein are cameras 240 and 242 positioned above reference substrate 244. The scanning cameras are mounted to assure that the adjacent scan bands 246, 248 affirmatively overlap. Periodic marks 250 are placed on the reference substrate to be scanned having, as an example, one or more rows of reference dots down the center of the medium. The location of the dots in the overlapping portions of the scan data are then compared to generate a correction factor for the adjacent band.

If only an axial displacement was present, the correction factor is simply additive to the pixel positions of the subsequent band. If more than two cameras are used, the correction factors is cumulatively additive for successive cameras. For example, the pixels scanned in the first band by the first camera are assumed to be in the correct positions. The correction factor (X1) calculated for the second camera is simply the difference between the axial position of a reference dot in the first band and the position of the same reference dot in the second band. The correction factor X1 is added to the X position of a reference dot in the second band and its corresponding position in the third band. The correction factor for a third camera is then X1 and X2, and is added to the X position of each pixel in the third band. A fourth camera would have a correction factor of equal to X1+X2+X3, etc.

Similar corrections are readily generated in the Y direction and corrections can be made for angular misalignment. The corrections could be made in the data following the scan, and thus do not have to be done in real time. The present system has increased throughput because of the addition of more scanning cameras without the need for elaborate alignment procedures in manufacture and during subsequent operation. The system could generate correction factors each time a workpiece is scanned or periodically, depending on the environment in which the machine operates.

The present system also is characterized by an apparatus for compensating for repeatable motion control error. As is known in the art, the mechanical components of every system are characterized by an accuracy value which is repeatable and is derived from the sum of the variations and accuracy of the various mechanical componentry such as ways, guides, etc. The present invention provides compensation by way of a table of compensation values generated during initial calibration. A reference substrate containing features spaced apart a known distance from one another is scanned by the present system. The controller computes the distances and compares the respective feature separations as measured with the correct values and determines a table of corrections to be applied to the commanded values for actual substrate features to assure correct placement.

The present compensation apparatus can also be employed with distorted artwork or panels which are distorted in a repeatable manner and if the substrates are registered (by a pin or its equivalent) in such a way that the substrate orientation is unique and unambiguous. For these situations, the regular distortion is ascertained as above, where the reference marks comprise, for example, a grid. Thereafter, the system applies a correction specific for those substrates (e.g., produced by the same imager) in addition to any other compensation that has been generated.

Similarly, although the invention has been shown and described with respect to a preferred embodiment thereof, it should be understood by those skilled in the art that various other changes, omissions and additions thereto may be made therein without departing from the spirit and scope of the present invention.

We claim:

1. A system for generating a tolerance database for use in the fabrication of PCB artwork, said system comprising:

a means for generating a nominal database of signals indicative of an image of printed circuit board (PCB) artwork features each having nominal dimensions, said databases comprised of an array of pixels having either a first state (black) or a second state (white), with said black state pixels corresponding to said PCB features;

a means for generating a database having signals corresponding to at least one set of minimum and maximum tolerance values for at least a selected one of said PCB features;

a means for providing a minimum database from said nominal and said tolerance value databases such that said selected PCB feature nominal dimensions are reduced by said minimum tolerance value;

a means for providing a maximum database from said nominal and said tolerance value databases such that said selected PCB feature nominal dimensions are increased by said maximum tolerance value;

a means for comparing the state of each of the pixels in said minimum database with said nominal pixel state;

a means for comparing the state of each of the pixels in said maximum database with said nominal pixel state;

a means for providing to a tolerance transition database a black state pixel if both of said minimum and maximum pixel states are black;

a means for providing to said tolerance transition database a white state pixel if both of said minimum and maximum pixel states are white;

a means for providing to said tolerance transition database a black transition state pixel if said minimum and nominal pixels are of different pixel states;

a means for providing to said tolerance transition database a white transition state pixel if said minimum and nominal pixels are of different pixel states;

a means for assigning each pixel a numerical weight in accord with its state;

a means for configuring said tolerance transition database into arrays of adjacent pixels;

a means for summing each of said pixel weights in a one of said pixel arrays; and a means for establishing a value of array pixels summed weight as a defect threshold;

a platen for receiving a substrate;

a carriage moveable relative to said substrate;

a means for moving said carriage relative to said substrate in response to received signals from a controller;

an optical source for providing an illumination optical beam;

an optical subassembly configured with said carriage for directing said illumination optical beam onto said substrate;

a camera positioned with said optical subassembly for receiving a portion of said illumination optical beam reflected from said substrate and providing electrical signal equivalents thereof;

a signal processing means for processing said camera signals into a scan database of pixel signals, said pixel having a either black or white state in accordance with the presence or absence, respectively, of a detected substrate feature;

a means for assigning each of said scan database pixels a numerical weight in accord with its state;

a means for configuring said scan database into arrays of adjacent pixels;

a means for summing each of said scan database pixel weights in a one of said scan data base pixel arrays;

a means for comparing said scan database array pixel summed weight against said defect threshold value; and a means for generating a signal indicative of a defect should said scan database array pixel summed weight exceed said defect threshold value;

said controller further comprising a means for moving said carriage relative to said substrate in a sequence of positions thereon in a serpentine manner, said camera generating corresponding sets of pixel signals for entry into said scan database;

said optical subsystem further comprising;

first and second cameras fixedly spaced from one another across a scan line on said substrate in respective substrate bands such that an overlap area of the substrate is imaged by both of said cameras;

identification means for determining pixel signals from both of said cameras which correspond to said overlap area; and compensation means for removing from said scan database redundant pixel signals from said overlap area.

2. The system of claim 1 wherein said identification means further generates correction signals by comparing the location of scanned reference marks within said overlap area with their corresponding known locations, and wherein said compensation means identifies pixel signals in said scanned database as redundant by comparison with said correction signals.

3. The system of claim 1 wherein said identification means generates correction signals by calculating the difference between a reference dot position in a first camera band and a corresponding reference dot position in a second band, and wherein said compensation means adds a corresponding correction signal to the position of each pixel signal.

4. A system for generating a tolerance database for use in the fabrication of PCB artwork, said system comprising:

a means for generating a nominal database of signals indicative of an image of printed circuit board (PCB) artwork features each having nominal dimensions, said databases comprised of an array of pixels having either a first state (black) or a second state (white), with said black state pixels corresponding to said PCB features;

a means for generating a database having signals corresponding to at least one set of minimum and maximum tolerance values for at least a selected one of said PCB features;

a means for providing a minimum database from said nominal and said tolerance value databases such that said selected PCB feature nominal dimensions are reduced by said minimum tolerance value;

a means for providing a maximum database from said nominal and said tolerance value databases such that said selected PCB feature nominal dimensions are increased by said maximum tolerance value;

a means for comparing the state of each of the pixels in said minimum database with said nominal pixel state;

a means for comparing the state of each of the pixels in said maximum database with said nominal pixel state;

a means for providing to a tolerance transition database a black state pixel if both of said minimum and maximum pixel states are black;

a means for providing to said tolerance transition database a white state pixel if both of said minimum and maximum pixel states are white;

a means for providing to said tolerance transition database a black transition state pixel if said minimum and nominal pixels are of different pixel states;

a means for providing to said tolerance transition database a white transition state pixel if said minimum and nominal pixels are of different pixel states;

a means for assigning each pixel a numerical weight in accord with its state;

a means for configuring said tolerance transition database into arrays of adjacent pixels;

a means for summing each of said pixel weights in a one of said pixel arrays; and a means for establishing a value of array pixels summed weight as a defect threshold;

a platen for receiving a substrate;

a carriage moveable relative to said substrate;

a means for moving said carriage relative to said substrate in response to received signals from a controller;

an optical source for providing an illumination optical beam;

an optical subassembly configured with said carriage for directing said illumination optical beam onto said substrate;

a camera positioned with said optical subassembly for receiving a portion of said illumination optical beam reflected from said substrate and providing electrical signal equivalents thereof;

a signal processing means for processing said camera signals into a scan database of pixel signals, said pixel having a either black or white state in accordance with the presence or absence, respectively, of a detected substrate feature;

a means for assigning each of said scan database pixels a numerical weight in accord with its state;

a means for configuring said scan database into arrays of adjacent pixels;

a means for summing each of said scan database pixel weights in a one of said scan database pixel arrays;

a means for comparing said scan database array pixel summed weight against said defect 'threshold value; and a means for generating a signal indicative of a defect should said scan database array pixel summed weight exceed said defect threshold value;

said optical subassembly further comprising an adaptive illumination means for maintaining a constant brightness of the illumination beam, said adaptive illumination means including;

a means for providing brightness control signals to said optical source;

a means for generating a histogram of pixel signal intensities at a reference illumination beam brightness;

a means for determining the total number of pixels in said histogram;

a threshold computation means for computing the number of said histogram pixels which comprise a selected percentage of the maximum pixel signal intensities and a pixel intensity grey scale value above which said maximum pixel signal intensities lie;

an averaging means for determining the average intensity of said selected percentage of the maximum pixel signal intensities;

a means for comparing said reference illumination beam brightness with a current illumination beam brightness and computing a brightness correction signal therefrom;

a means for generating a new brightness control signal from said current brightness control signal and said brightness correction signal.

5. The system of claim 4 wherein said threshold computation means further comprises a means for computing said threshold in accordance with the following:

Threshold=(int)(fraction * (double(n));

where fraction is equal to 0.05 and n is equal to the sum of all histogram intervals.

6. The system of claim 4 wherein said averaging means further comprises a means for computing said average intensity above the selected percentage value in accordance with the following:

```
cumm = 0;
avg = 0;
for (i = 225, i >= 0; --i)
{
cumm += hist[i];
avg += (long)hist[i] * (long)i;
if (cumm >= threshold)
  break;
}
max_average = (int) (avg/(long)cumm);
``` where "cumm" is the grey scale value and "avg" is an average intensity.

7. The system of claim 4 wherein said new brightness control signal is computed in accordance with the following:

$$1_{t+1}=K * correction * 1_t+(1-K) * 1_t$$

where "$1_t$" corresponding to the current brightness control signal value at time t, "correction corresponds to the value of the brightness correction signal and "K" is an empirically determined constant.

8. A system for generating a tolerance database for use in the fabrication of PCB artwork, said system comprising:

a means for generating a nominal database of signals indicative of an image of printed circuit board (PCB) artwork features each having nominal dimensions, said databases comprised of an array of pixels having either a first state (black) or a second state (white), with said black state pixels corresponding to said PCB features;

a means for generating a database having signals corresponding to at least one set of minimum and maximum tolerance values for at least a selected one of said PCB features;

a means for providing a minimum database from said nominal and said tolerance value databases such that said selected PCB feature nominal dimensions are reduced by said minimum tolerance value;

a means for providing a maximum database from said nominal and said tolerance value databases such that said selected PCB feature nominal dimensions are increased by said maximum tolerance value;

a means for comparing the state of each of the pixels in said minimum database with said nominal pixel state;

a means for comparing the state of each of the pixels in said maximum database with said nominal pixel state;

a means for providing to a tolerance transition database a black state pixel if both of said minimum and maximum pixel states are black;

a means for providing to said tolerance transition database a white state pixel if both of said minimum and maximum pixel states are white;

a means for providing to said tolerance transition database a black transition state pixel if said minimum and nominal pixels are of different pixel states;

a means for providing to said tolerance transition database a white transition state pixel if said minimum and nominal pixels are of different pixel states;

a means for assigning each pixel a numerical weight in accord with its state;

a means for configuring said tolerance transition database into arrays of adjacent pixels;

a means for summing each of said pixel weights in a one of said pixel arrays; and a means for establishing a value of array pixels summed weight as a defect threshold;

a platen for receiving a substrate;

a carriage moveable relative to said substrate;

a means for moving said carriage relative to said substrate in response to received signals from a controller;

an optical source for providing an illumination optical beam;

an optical subassembly configured with said carriage for directing said illumination optical beam onto said substrate;

a camera positioned with said optical subassembly for receiving a portion of said illumination optical beam reflected from said substrate and providing electrical signal equivalents thereof;

a signal processing means for processing said camera signals into a scan database of pixel signals, said pixel having a either black or white state in accordance with the presence or absence, respectively, of a detected substrate feature;

a means for assigning each of said scan database pixels a numerical weight in accord with its state;

a means for configuring said scan database into arrays of adjacent pixels;

a means for summing each of said scan database pixel weights in a one of said scan database pixel arrays;

a means for comparing said scan database array pixel summed weight against said defect threshold value; and a means for generating a signal indicative of a defect should said scan database array pixel summed weight exceed said defect threshold value;

said signal processing means further comprising;

a means for providing compensation for defects in the optical subsystem, including;

a means for creating a pixel database of calibration artwork imaged by said optical subsystem;

a means for measuring the relative positions of registration marks in said calibration artwork pixel database;

a means for comparing said measured registration marks relative positions with ideal relative positions;

a means for computing optical defect compensation signals in dependence on said comparison;

a means for providing compensation for substrate distortion, including;

a means for identifying in a scan database pixel signals corresponding to registration marks imaged on said substrate;

a means for computing the position of said scanned substrate registration marks relative to one another;

a means for comparing said computed registration mark relative positions with ideal relative positions;

a means for computing substrate distortion pixel placement compensation signals in dependence on said comparison;

a means for providing compensation for repeatable motion control error, including;

a means for creating a scanned pixel database of a registration substrate having a sequence of registration marks therein;

a means for measuring the relative positions of said registration marks in said registration substrate;

a means for comparing said measured registration marks relative positions with ideal relative positions;

a means for computing motion control pixel placement compensation signals in dependence on said comparison; and a means for combining said computed motion control compensation signals with said computed optical defect compensation signals with said computed substrate distortion compensation signals, all with said scanned database signals to remove any differences in pixel placement as compared to ideal locations, thereby removing system error.

9. The system of claim 8 wherein said compensation signals are stored with said processor means in a look up table format.

10. The system of claim 8 further comprising marker means affixed to said carriage for providing a mark adjacent each identified defect.

11. An apparatus for generating a tolerance database from a nominal database of signals indicative of an image of printed circuit board (PCB) artwork features each having nominal dimensions, said databases comprised of an array of pixels having either a first state (black) or a second state (white), with said black state pixels corresponding to said PCB features said apparatus comprising:

a means for generating a database having signals corresponding to at least one set of minimum and maximum tolerance values for at least a selected one of said PCB features;

a means for providing a minimum database from said nominal and said tolerance value databases such that said selected PCB feature nominal dimensions are reduced by said minimum tolerance value;

a means for providing a maximum database from said nominal and said tolerance value databases such that said selected PCB feature nominal dimensions are increased by said maximum tolerance values;

a means for comparing the state of each of the pixels in said minimum database with said nominal pixel state;

a means for comparing the state of each of the pixels in said maximum database with said nominal pixel state;

a means for providing to a tolerance transition database a black state pixel if both of said minimum and maximum pixel states are black;

a means for providing to said tolerance transition database a white state pixel if both of said minimum and maximum pixel states are white;

a means for providing to said tolerance transition database a black transition state pixel if said minimum and nominal pixels are of different pixel states;

a means for providing to said tolerance transition database a white transition state pixel if said maximum and nominal pixels are of different pixel states;

a means for assigning each pixel a numerical weight in accord with its state;

a means for configuring said tolerance transition database into arrays of adjacent pixels;

a means for summing each of said pixel weights in a one of said pixel arrays;

a means for establishing a value of array pixel summed weight as a defect threshold; and a means for configuring said arrays to overlap in pixel elements.

12. An apparatus for generating a tolerance database from a nominal database of signals indicative of an image of printed circuit board (PCB) artwork features each having nominal dimensions, said databases comprised of an array of pixels having either a first state (black) or a second state (white), with said black state pixels corresponding to said PCB features said apparatus comprising:

a means for generating a database having signals corresponding to at least one set of minimum and maximum tolerance values for at least a selected one of said PCB features;

a means for providing a minimum database from said nominal and said tolerance value databases such that said selected PCB feature nominal dimensions are reduced by said minimum tolerance value;

a means for providing a maximum database from said nominal and said tolerance value databases such that said selected PCB feature nominal dimensions are increased by said maximum tolerance values;

a means for comparing the state of each of the pixels in said minimum database with said nominal pixel state;

a means for comparing the state of each of the pixels in said maximum database with said nominal pixel state;

a means for providing to a tolerance transition database a black state pixel if both of said minimum and maximum pixel states are black;

a means for providing to said tolerance transition database a white state pixel if both of said minimum and maximum pixel states are white;

a means for providing to said tolerance transition database a black transition state pixel if said minimum and nominal pixels are of different pixel states;

a means for providing to said tolerance transition database a white transition state pixel if said maximum and nominal pixels are of different pixel states;

a means for assigning each pixel a numerical weight in accord with its state;

a means for configuring said tolerance transition database into arrays of adjacent pixels;

a means for summing each of said pixel weights in a one of said pixel arrays;

a means for establishing a value of array pixel summed weight as a defect threshold; and a means for convolving the sum of said defect weights for an array with the defect weights of each adjacent array when the pixels of said arrays are unique.

13. An apparatus for generating a tolerance database from a nominal database of signals indicative of an image of printed circuit board (PCB) artwork features each having nominal dimensions, said databases comprised of an array of pixels having either a first state (black) or a second state (white), with said black state pixels corresponding to said PCB features said apparatus comprising:

a means for generating a database having signals corresponding to at least one set of minimum and maximum tolerance values for at least a selected one of said PCB features;

a means for providing a minimum database from said nominal and said tolerance value databases such that said selected PCB feature nominal dimensions are reduced by said minimum tolerance value;

a means for providing a maximum database from said nominal and said tolerance value databases such that said selected PCB feature nominal dimensions are increased by said maximum tolerance values;

a means for comparing the state of each of the pixels in said minimum database with said nominal pixel state;

a means for comparing the state of each of the pixels in said maximum database with said nominal pixel state;

a means for providing to a tolerance transition database a black state pixel if both of said minimum and maximum pixel states are black;

a means for providing to said tolerance transition database a white state pixel if both of said minimum and maximum pixel states are white;

a means for providing to said tolerance transition database a black transition state pixel if said minimum and nominal pixels are of different pixel states;

a means for providing to said tolerance transition database a white transition state pixel if said maximum and nominal pixels are of different pixel states;

means for assigning each pixel a numerical weight in accord with its state;

a means for configuring said tolerance transition database into arrays of adjacent pixels;

a means for summing each of said pixel weights in a one of said pixel arrays;

a means for establishing a value of array pixel summed weight as a defect threshold; and a means for consolidating the defect weight of adjacent cells to form a single large cell having an aggregate defect weight.

14. A system for generating a tolerance database for use in the fabrication of PCB artwork, said system comprising:

a means for generating a nominal database of signals indicative of an image of printed circuit board (PCB) artwork features each having nominal dimensions said databases comprised of an array of pixels having either a first state (black) or a second state (white), with said black state pixels corresponding to said PCB features;

a means for generating a database having signals corresponding to at least one set of minimum and maximum tolerance values for at least a selected one of said PCB features;

a means for providing a minimum database from said nominal and said tolerance value databases such that said selected PCB feature nominal dimensions are reduced by said minimum tolerance value;

a means for providing a maximum database from said nominal and said tolerance value databases such that said selected PCB feature nominal dimensions are increased by said maximum tolerance value;

a means for comparing the state of each of the pixels in said minimum database with said nominal pixel state;

a means for comparing the state of each of the pixels in said maximum database with said nominal pixel state;

a means for providing to a tolerance transition database a black state pixel if both of said minimum and maximum pixel states are black;

a means for providing to said tolerance transition database a white state pixel if both of said minimum and maximum pixel states are white;

a means for providing to said tolerance transition database a black transition state pixel if said minimum and nominal pixels are of different pixel states;

a means for providing to said tolerance transition database a white transition state pixel if said minimum and nominal pixels are of different pixel a means for assigning each pixel a numerical weight in accord with its state;

a means for configuring said tolerance transition database into arrays of adjacent pixels;

a means for summing each of said pixel weights in a one of said pixel arrays;

a means for establishing a value of array pixels summed weight as a defect threshold;

a platen for receiving a substrate;

a carriage moveable relative to said substrate;

a means for moving said carriage relative to said substrate in response to received signals from a controller;

on optical source for providing an illumination optical beam;

an optical subassembly configured with said carriage for directing said illumination optical beam onto said substrate;

a camera positioned with said optical subassembly for receiving a portion of said illumination optical beam reflected from said substrate and providing electrical signal equivalents thereof;

a signal processing means for processing said camera signals into a scan database of pixel signals said pixel having a either black or white state in accordance with the presence or absence respectively, of a detected substrate feature;

a means for assigning each of said scan database pixels a numerical weight in accord with its state;

a means for configuring said scan database into arrays of adjacent pixels;

a means for summing each of said scan database pixel weights in a one of said scan database pixel arrays;

a means for comparing said scan database array pixel summed weight against said defect threshold value;

a means for generating a signal indicative of a defect should said scan database array pixel summed weight exceed said defect threshold value;

a locating means for providing repeatable positioning of a substrate on said platen; and a means for classifying said pixel signals by first comparing said pixel signals with a median level threshold to divide said pixel database into upper and lower pixel signal value magnitude classes and thereafter comparing said upper magnitude class with a upper level threshold and said lower magnitude class a lower level threshold to classify each pixel into one or four states.

15. A system for generating a tolerance database for use in the fabrication of PCB artwork, said system comprising;

a means for generating a nominal database of signals indicative of an image of printed circuit board (PCB) artwork features each having nominal dimensions, said databases comprised of an array of pixels having either a first state (black) or a second state (white), with said black state pixels corresponding to said PCB features;

a means for generating a database having signals corresponding to at least one set of minimum and maximum tolerance values for at least a selected one of said PCB features;

a means for providing a minimum database from said nominal and said tolerance value databases such that said selected PCB feature nominal dimensions are reduced by said minimum tolerance value;

a means for providing a maximum database from said nominal and said tolerance value databases such that said selected PCB feature nominal dimensions are increased by said maximum tolerance value;

a means for comparing the state of each of the pixels in said minimum database with said nominal pixel state;

a means for comparing the state of each of the pixels in said maximum database with said nominal pixel state;

a means for providing to a tolerance transition database a black state pixel if both of said minimum and maximum pixel states are black;

a means for providing to said tolerance transition database a white state pixel if both of said minimum and maximum pixel states are white;

a means for providing to said tolerance transition database a black transition state pixel if said minimum and nominal pixels are of different pixel states;

a means for providing to said tolerance transition database a white transition state pixel if said minimum and nominal pixels are of different pixel states;

a means for assigning each pixel a numerical weight in accord with its state;

a means for configuring said tolerance transition database into arrays of adjacent pixels;

a means for summing each of said pixel weights in a one of said pixel arrays;

a means for establishing a value of array Pixels summed weight as a defect threshold;

a platen for receiving a substrate;

a carriage moveable relative to said substrate;

a means for moving said carriage relative to said substrate in response to received signals from a controller;

an optical source for providing an illumination optical beam;

an optical subassembly configured with said carriage for directing said illumination optical beam onto said substrate;

a camera positioned with said optical subassembly for receiving a portion of said illumination optical beam reflected from said substrate and providing electrical signal equivalents thereof;

a signal processing means for processing said camera signals into a scan database of pixel signals, said pixel having a either black or white state in accordance with the presence or absence respectively of a detected substrate feature;

a means for assigning each of said scan database pixels a numerical weight in accord with its state;

a means for configuring said scan database into arrays of adjacent pixels;

a means for summing cinch of said scan database pixel weights in a one of said scan database pixel arrays;

a means for completing said scan database array pixel summed weight against said defect threshold value; and a means for generating a signal indicative of a defect should said scan database pixel summed weight exceed said defect threshold value;

a locating means for providing repeatable positioning of a substrate on said platen;

a means for converting said tolerance transition database and said scan databases into a compressed format;

a means for comparing said compressed scan database with said compressed tolerance transition database and generating a defect signal therefrom; and a means for assigning said pixel weights after said comparison of said compressed scan database with said compressed tolerance transition database.

16. A system for generating a tolerance database for use in the fabrication of PCB artwork, said system comprising:

a means for generating a nominal database of signals indicative of an image of printed circuit board (PCB) artwork features each having nominal dimensions, said databases comprised of an array of pixels having either a first state (black) or a second state (white), with said black state pixels corresponding to said PCB features;

a means for generating a database having signals corresponding to at least one set of minimum and maximum tolerance values for at least a selected one of said PCB features;

a means for providing a minimum database from said nominal and said tolerance value databases such that said selected PCB feature nominal dimensions are reduced by said minimum tolerance value;

a means for providing a maximum database from said nominal and said tolerance value databases such that said selected PCB feature nominal dimensions are increased by said maximum tolerance value;

a means for comparing the state of each of the pixels in said minimum database with said nominal pixel state;

a means for comparing the state of each of the pixels in said maximum database with said nominal pixel state;

a means for providing to a tolerance transition database a black state pixel if both of said minimum and maximum pixel states are black;

a means for providing to said tolerance transition database a white state pixel if both of said minimum and maximum pixel states are white;

a means for providing to said tolerance transition database a black transition state pixel if said minimum and nominal pixels are of different pixel states;

a means for providing to said tolerance transition database a white transition state pixel if said minimum and nominal pixels are of different pixel states;

a means for assigning each pixel a numerical weight in accord with its state;

means for configuring said tolerance transition database into arrays of adjacent pixels;

a means for summing each of said pixel weights in a one of said pixel arrays; and a means for establishing a value of array pixels summed weight as a defect threshold;

a platen for receiving a substrate;

a carriage moveable relative to said substrate;

a means for moving said carriage relative to said substrate in response to received signals from a controller;

an optical source for providing an illumination optical beam;

an optical subassembly configured with said carriage for directing said illumination optical beam onto said substrate;

a camera positioned with said optical subassembly for receiving a portion of said illumination optical beam reflected from said substrate and providing electrical signal equivalents thereof;

a signal processing means for processing said camera signals into a scan database of pixel signals, said pixel having a either black or white state in accordance with the presence or absence, respectively, of a detected substrate feature;

a means for assigning each of said scan database pixels a numerical weight in accord with its state;

a means for configuring said scan database into arrays of adjacent pixels;

a means for summing each of said scan database pixel weights in a one of said scan database pixel arrays;

a means for comparing said scan database array pixel summed weight against said defect threshold value; and a means for generating a signal indicative of a defect should said scan database array pixel summed weight exceed said defect threshold value;

said signal processing means further comprising sample interpolation means including;

a means for determining an intensity value for adjacent pairs of said scanned pixel signals;

a means for computing an average intensity value of said adjacent scanned pixel signal pairs;

a means for computing an intermediate pixel signal positioned between said scanned pixel pair having an intensity value corresponding to an average intensity value, thereby increasing a scanned database pixel density.

* * * * *